United States Patent
Teufel et al.

(10) Patent No.: US 10,894,808 B2
(45) Date of Patent: *Jan. 19, 2021

(54) POLYPEPTIDE LIGANDS SPECIFIC FOR PLASMA KALLIKREIN

(71) Applicant: BicycleRD Limited, Cambridge (GB)

(72) Inventors: Daniel Teufel, Cambridge (GB); Catherine Stace, Cambridge (GB); Edward Walker, Cambridge (GB)

(73) Assignee: BicycleRD Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,264

(22) Filed: Jan. 3, 2019

(65) Prior Publication Data

US 2019/0233475 A1   Aug. 1, 2019

Related U.S. Application Data

(63) Continuation of application No. 15/029,248, filed as application No. PCT/GB2014/053199 on Oct. 28, 2014, now Pat. No. 10,294,274.

(30) Foreign Application Priority Data

Oct. 28, 2013 (GB) .................................. 1318941
Jun. 10, 2014 (GB) .................................. 1410265.1

(51) Int. Cl.
  *C07K 7/64* (2006.01)
  *C07K 7/08* (2006.01)
  *C07K 17/00* (2006.01)
  *A61K 38/00* (2006.01)

(52) U.S. Cl.
  CPC .................. *C07K 7/64* (2013.01); *C07K 7/08* (2013.01); *C07K 17/00* (2013.01); *A61K 38/00* (2013.01)

(58) Field of Classification Search
  None
  See application file for complete search history.

(56) References Cited

U.S. PATENT DOCUMENTS

| | | | | |
|---|---|---|---|---|
| 10,294,274 | B2 * | 5/2019 | Teufel | .................... C07K 17/00 |
| 2008/0313749 | A1 | 12/2008 | Timmerman et al. | |
| 2010/0317547 | A1 | 12/2010 | Gregory et al. | |

FOREIGN PATENT DOCUMENTS

| | | |
|---|---|---|
| EP | 2474613 | 7/2014 |
| WO | 2006078161 | 7/2006 |
| WO | 2009098450 | 8/2009 |
| WO | 2010089115 | 8/2010 |
| WO | 2013050615 | 4/2013 |
| WO | 2013050616 | 4/2013 |
| WO | 2013050617 | 4/2013 |
| WO | 2014140342 | 9/2014 |
| WO | 2014167122 | 10/2014 |

OTHER PUBLICATIONS

Baeriswyl et al. "Bicyclic Peptides with Optimized Ring Size Inhibit Human Plasma Kallikrein and its Orthologues While Sparing Paralogous Proteases" ChemMedChem 7:1173-1176 (Year: 2012).*
Anonymous "Free Modifications: N-Terminal Acetylation adn C-Terminal Amidation" LifeTein https://www.lifetein.com/Peptide-Synthesis-Amidation-Acetylation.html. (Year: 2012).*
Anonymous "What are the various salt forms of peptides?" https://www.biosyn.com/faq/what-are-the-various-salt-forms-of-peptides.aspx (Year: 2009).*
Appel et al., "Characterization of antigen-antibody interactions using single substitution analogs and mixture-based synthetic combinatorial libraries," Chemical Biology & Drug Discovery, vol. 52, No. 5, Nov. 1998 (pp. 346-355).
Burgess et al., "DiSSiMiL: Diverse Small Size Mini-Libraries applied to simple and rapid epitope mapping of a monoclonal antibody," Journal of Peptide Research, vol. 57, No. 1, Jan. 2001 (pp. 68-76).
International Search Report and Written Opinion issued by the European Patent Office as International Searching Authority for International Application No. PCT/GB2014/053199 dated Jul. 16, 2015 (17 pages).

* cited by examiner

*Primary Examiner* — Larry D Riggs, II
*Assistant Examiner* — Zachary J Miknis
(74) *Attorney, Agent, or Firm* — Andrea L. C. Reid; Dechert LLP

(57) ABSTRACT

The present invention relates to polypeptides which are covalently bound to molecular scaffolds such that two or more peptide loops are subtended between attachment points to the scaffold. In particular, the invention describes peptides which are specific for the human and rat protease plasma kallikrein and are modified in one or two peptide loops to enhance potency and/or protease resistance.

42 Claims, 11 Drawing Sheets

Specification includes a Sequence Listing.

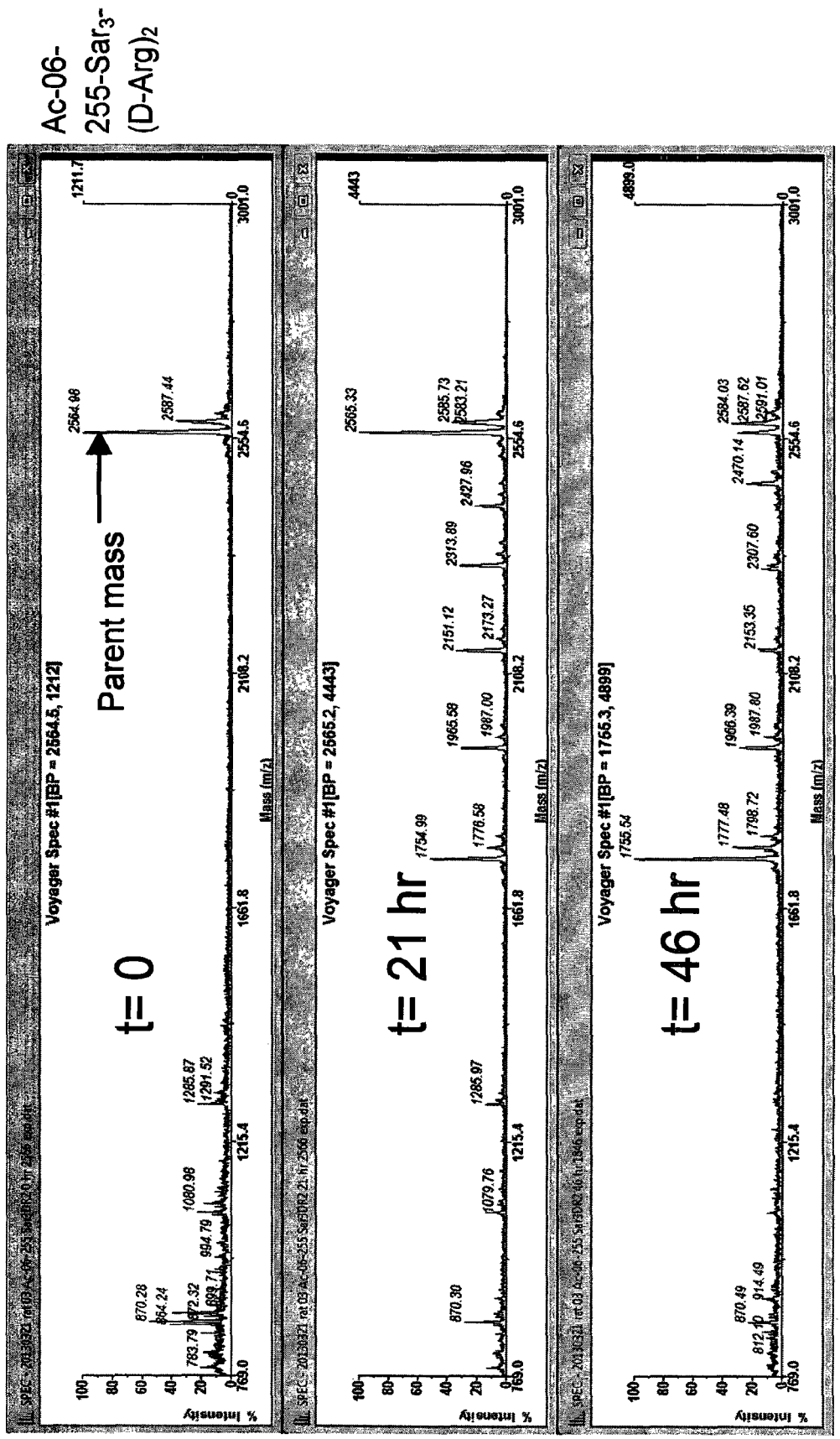
FIGURE 1 (ctd)

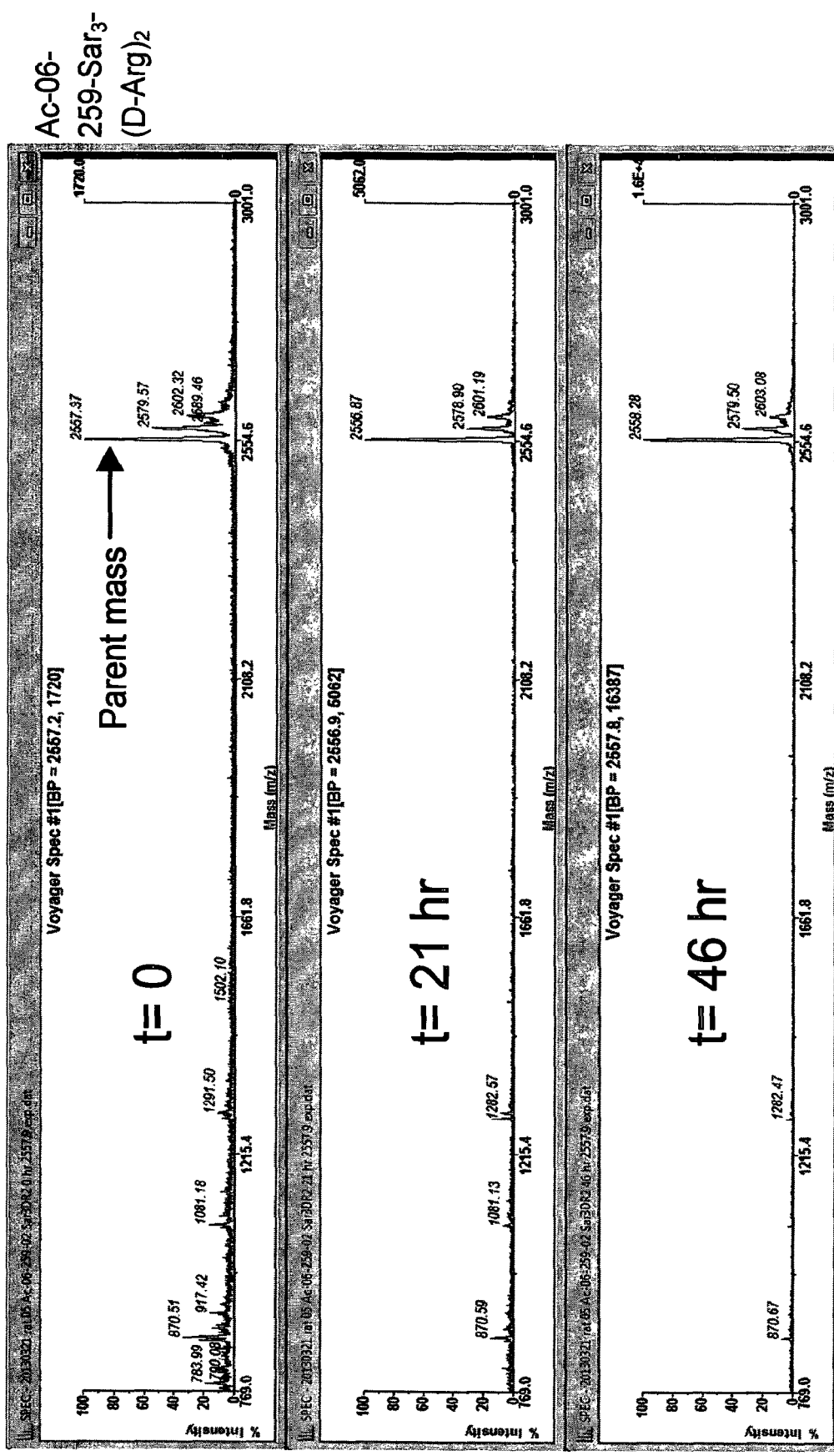
FIGURE 1 (ctd)

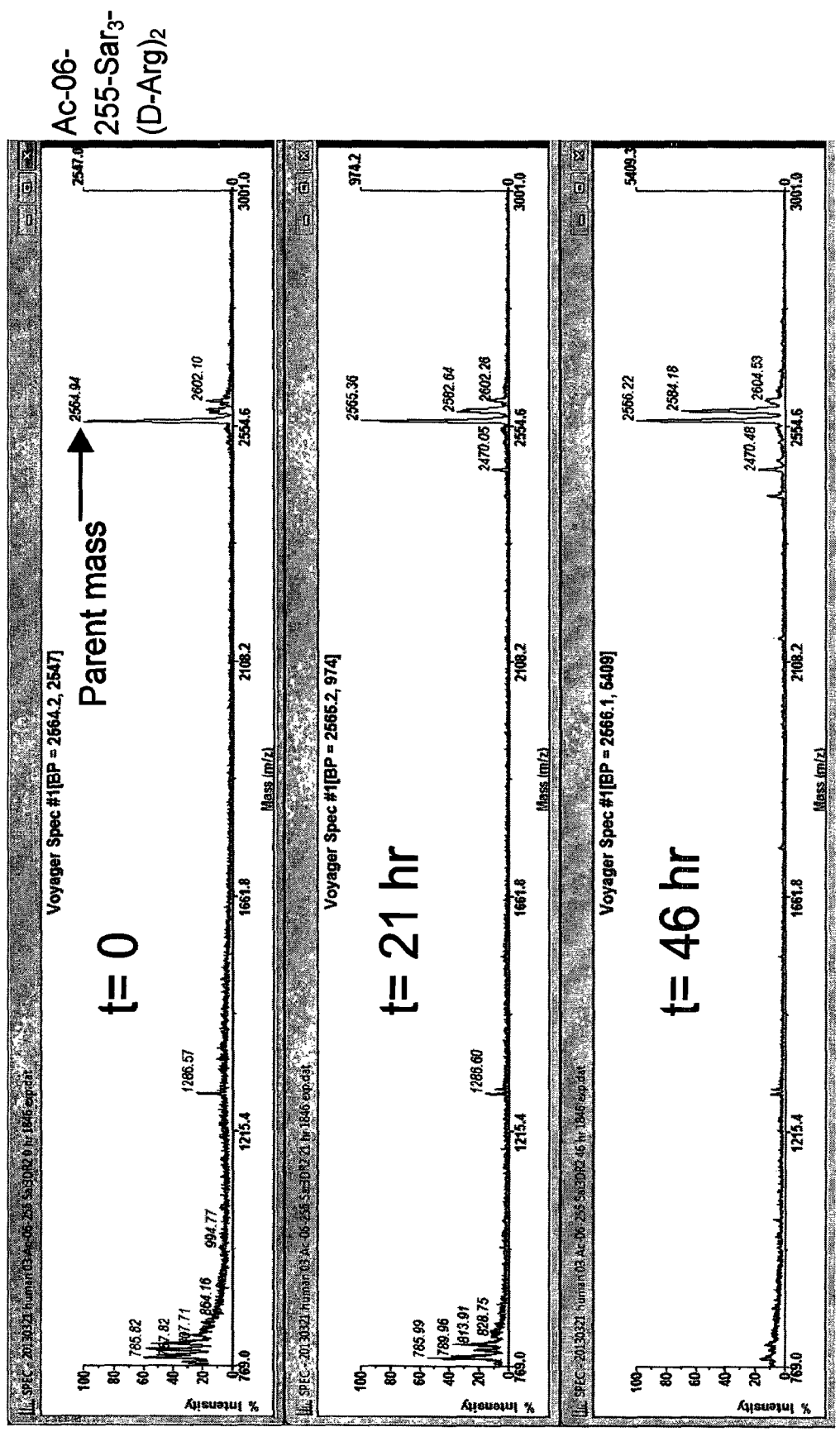
FIGURE 2 (ctd)

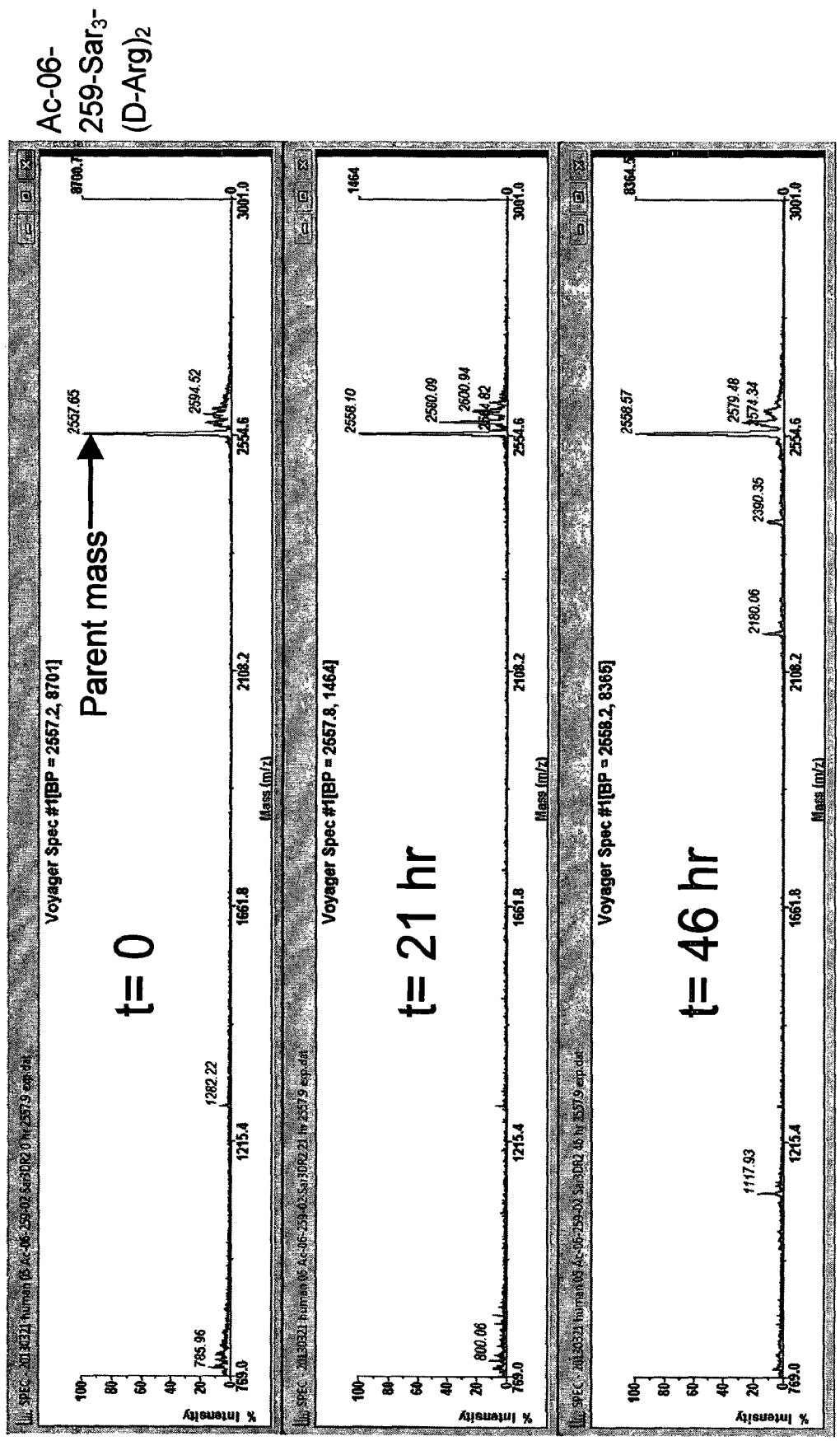
FIGURE 2 (ctd)

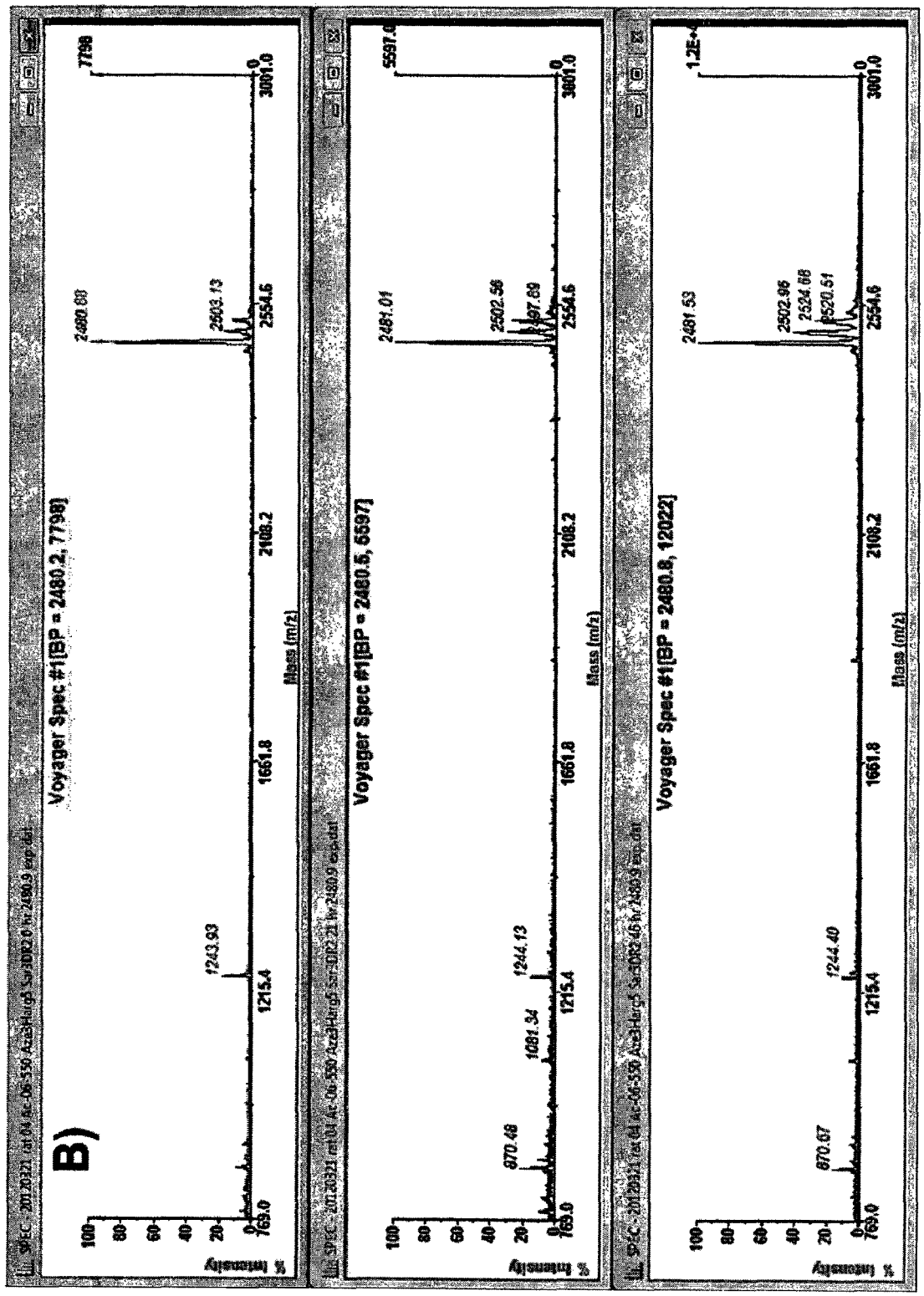
FIGURE 3 (ctd)

SEQUENCE LISTING

```
<160> NUMBER OF SEQ ID NOS: 100

<210> SEQ ID NO 1
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (3)..(3)
<223> OTHER INFORMATION: Xaa represents any amino acid residue
<220> FEATURE:
<221> NAME/KEY: MISC_FEATURE
<222> LOCATION: (9)..(9)
<223> OTHER INFORMATION: Xaa represents either a non-polar aliphatic
      amino acid residue selected from G, A, I, L, P and V or a polar,
      uncharged amino acid residue selected from N, C, Q, M, S and T
<220> FEATURE:
<221> NAME/KEY: MISC_FEATURE
<222> LOCATION: (10)..(12)
<223> OTHER INFORMATION: Xaa represents any amino acid residue
<220> FEATURE:
<221> NAME/KEY: MISC_FEATURE
<222> LOCATION: (13)..(13)
<223> OTHER INFORMATION: Xaa represents either a non-polar aliphatic
      amino acid residue selected from G, A, I, L, P and V or a
      non-polar aromatic amino acid residue selected from F, W and Y
<220> FEATURE:
<221> NAME/KEY: MISC_FEATURE
<222> LOCATION: (14)..(14)
<223> OTHER INFORMATION: Xaa represents any amino acid residue

<400> SEQUENCE: 1

Cys Asn Xaa Trp Asn Pro Trp Cys Xaa Xaa Xaa Xaa Xaa Xaa Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents a polar, positively charged
      amino acid residue selected from R, H and K
<220> FEATURE:
<221> NAME/KEY: MISC_FEATURE
<222> LOCATION: (4)..(4)
<223> OTHER INFORMATION: Xaa represents a non-polar aromatic amino acid
      residue selected from F, W and Y
<220> FEATURE:
<221> NAME/KEY: MISC_FEATURE
<222> LOCATION: (9)..(9)
<223> OTHER INFORMATION: Xaa represents any amino acid residue
<220> FEATURE:
```

```
<221> NAME/KEY: MISC_FEATURE
<222> LOCATION: (11)..(11)
<223> OTHER INFORMATION: Xaa represents a non-polar aliphatic amino acid
      residue selected from G, A, I, L, P and V
<220> FEATURE:
<221> NAME/KEY: MISC_FEATURE
<222> LOCATION: (12)..(14)
<223> OTHER INFORMATION: Xaa represents any amino acid residue

<400> SEQUENCE: 2

Cys Xaa Asn Xaa Trp Asn Pro Cys Xaa Leu Xaa Xaa Xaa Xaa Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (9)..(14)
<223> OTHER INFORMATION: Xaa represents any amino acid residue

<400> SEQUENCE: 3

Cys Gln Lys Phe Glu Ser Arg Cys Xaa Xaa Xaa Xaa Xaa Xaa Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide ligand

<400> SEQUENCE: 4

Cys Pro Leu Ser Asp Thr Leu Cys Tyr Arg Arg Met Pro Pro Cys
1               5                   10                  15

<210> SEQ ID NO 5
<211> LENGTH: 13
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (8)..(8)
<223> OTHER INFORMATION: Xaa represents any amino acid residue
<220> FEATURE:
<221> NAME/KEY: MISC_FEATURE
<222> LOCATION: (10)..(12)
<223> OTHER INFORMATION: Xaa represents any amino acid residue

<400> SEQUENCE: 5

Cys Pro Tyr Pro Phe Arg Cys Xaa His Xaa Xaa Xaa Cys
1               5                   10

<210> SEQ ID NO 6
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents either no amino acid residue or
      one N residue
<220> FEATURE:
<221> NAME/KEY: MISC_FEATURE
```

```
<222> LOCATION: (3)..(3)
<223> OTHER INFORMATION: Xaa represents a polar, uncharged amino acid
      residue selected from N, C, Q, M, S and T
<220> FEATURE:
<221> NAME/KEY: MISC_FEATURE
<222> LOCATION: (4)..(4)
<223> OTHER INFORMATION: Xaa represents a non-polar aromatic amino acid
      residue selected from F, W and Y
<220> FEATURE:
<221> NAME/KEY: MISC_FEATURE
<222> LOCATION: (6)..(6)
<223> OTHER INFORMATION: Xaa represents a non-polar aromatic amino acid
      residue selected from F, W and Y

<400> SEQUENCE: 6

Cys Xaa Xaa Xaa Pro Xaa Arg Cys Val Tyr Tyr Pro Asp Ile Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (3)..(3)
<223> OTHER INFORMATION: Xaa represents any amino acid residue
<220> FEATURE:
<221> NAME/KEY: MISC_FEATURE
<222> LOCATION: (9)..(9)
<223> OTHER INFORMATION: Xaa represents either a non-polar aliphatic
      amino acid residue selected from G, A, I, L, P and V or a polar,
      uncharged amino acid residue selected from N, C, Q, M, S and T
<220> FEATURE:
<221> NAME/KEY: MISC_FEATURE
<222> LOCATION: (10)..(12)
<223> OTHER INFORMATION: Xaa represents any amino acid residue
<220> FEATURE:
<221> NAME/KEY: MISC_FEATURE
<222> LOCATION: (13)..(13)
<223> OTHER INFORMATION: Xaa represents a non-polar aliphatic amino acid
      residue selected from G, A, I, L, P and V
<220> FEATURE:
<221> NAME/KEY: MISC_FEATURE
<222> LOCATION: (14)..(14)
<223> OTHER INFORMATION: Xaa represents any amino acid residue

<400> SEQUENCE: 7

Cys Asn Xaa Trp Asn Pro Trp Cys Xaa Xaa Xaa Xaa Xaa Xaa Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (3)..(3)
<223> OTHER INFORMATION: Xaa represents T, H or Y
<220> FEATURE:
<221> NAME/KEY: MISC_FEATURE
<222> LOCATION: (9)..(9)
<223> OTHER INFORMATION: Xaa represents G, S or P
<220> FEATURE:
<221> NAME/KEY: MISC_FEATURE
<222> LOCATION: (10)..(10)
<223> OTHER INFORMATION: Xaa represents A, V, W, D or S
<220> FEATURE:
<221> NAME/KEY: MISC_FEATURE
<222> LOCATION: (11)..(11)
<223> OTHER INFORMATION: Xaa represents D, E, V, T or P
<220> FEATURE:
```

```
<221> NAME/KEY: MISC_FEATURE
<222> LOCATION: (12)..(12)
<223> OTHER INFORMATION: Xaa represents A, G, P, I, R or D
<220> FEATURE:
<221> NAME/KEY: MISC_FEATURE
<222> LOCATION: (13)..(13)
<223> OTHER INFORMATION: Xaa represents G, P, Y or I
<220> FEATURE:
<221> NAME/KEY: MISC_FEATURE
<222> LOCATION: (14)..(14)
<223> OTHER INFORMATION: Xaa represents F, I, L, V, R, G or D

<400> SEQUENCE: 8

Cys Asn Xaa Trp Asn Pro Trp Cys Xaa Xaa Xaa Xaa Xaa Xaa Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (3)..(3)
<223> OTHER INFORMATION: Xaa represents T, H or Y
<220> FEATURE:
<221> NAME/KEY: MISC_FEATURE
<222> LOCATION: (9)..(9)
<223> OTHER INFORMATION: Xaa represents G, S or P
<220> FEATURE:
<221> NAME/KEY: MISC_FEATURE
<222> LOCATION: (10)..(10)
<223> OTHER INFORMATION: Xaa represents A, V or W
<220> FEATURE:
<221> NAME/KEY: MISC_FEATURE
<222> LOCATION: (11)..(11)
<223> OTHER INFORMATION: Xaa represents D, E or V
<220> FEATURE:
<221> NAME/KEY: MISC_FEATURE
<222> LOCATION: (12)..(12)
<223> OTHER INFORMATION: Xaa represents A, G or P
<220> FEATURE:
<221> NAME/KEY: MISC_FEATURE
<222> LOCATION: (13)..(13)
<223> OTHER INFORMATION: Xaa represents G or P
<220> FEATURE:
<221> NAME/KEY: MISC_FEATURE
<222> LOCATION: (14)..(14)
<223> OTHER INFORMATION: Xaa represents F, I, L or V

<400> SEQUENCE: 9

Cys Asn Xaa Trp Asn Pro Trp Cys Xaa Xaa Xaa Xaa Xaa Xaa Cys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide ligand

<400> SEQUENCE: 10

Cys Asn Thr Trp Asn Pro Trp Cys Gly Trp Val Gly Gly Phe Cys
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide ligand
```

```
<400> SEQUENCE: 11

Cys Asn His Trp Asn Pro Trp Cys Ser Val Glu Pro Pro Val Cys
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide ligand

<400> SEQUENCE: 12

Cys Asn Thr Trp Asn Pro Trp Cys Pro Trp Asp Ala Pro Leu Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide ligand

<400> SEQUENCE: 13

Cys Asn His Trp Asn Pro Trp Cys Ser Ala Asp Pro Pro Ile Cys
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide ligand

<400> SEQUENCE: 14

Cys Asn Tyr Trp Asn Pro Trp Cys Pro Trp Asp Ala Pro Leu Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic peptide ligand

<400> SEQUENCE: 15

Cys Asn His Trp Asn Pro Trp Cys Ser Ala Asp Pro Pro Arg Cys
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic peptide ligand

<400> SEQUENCE: 16

Cys Asn His Trp Asn Pro Trp Cys Pro Ala Asp Ile Pro Val Cys
1               5                   10                  15

<210> SEQ ID NO 17
<211> LENGTH: 15
<212> TYPE: PRT
<213> ORGANISM: Artificial
<220> FEATURE:
<223> OTHER INFORMATION: Synthetic peptide ligand

<400> SEQUENCE: 17
```

Cys Asn His Trp Asn Pro Trp Cys Ser Asp Asp Pro Tyr Ile Cys
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthetic peptide ligand

<400> SEQUENCE: 18

Cys Asn His Trp Asn Pro Trp Cys Ser Ser Asp Pro Pro Val Cys
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic peptide ligand

<400> SEQUENCE: 19

Cys Asn Tyr Trp Asn Pro Trp Cys Ser Asp Thr Arg Ile Gly Cys
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic peptide ligand

<400> SEQUENCE: 20

Cys Asn Thr Trp Asn Pro Trp Cys Ser Trp Pro Asp Ile Asp Cys
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents K or R
<220> FEATURE:
<221> NAME/KEY: MISC_FEATURE
<222> LOCATION: (9)..(9)
<223> OTHER INFORMATION: Xaa represents D, T or G
<220> FEATURE:
<221> NAME/KEY: MISC_FEATURE
<222> LOCATION: (11)..(11)
<223> OTHER INFORMATION: Xaa represents I, V or L
<220> FEATURE:
<221> NAME/KEY: MISC_FEATURE
<222> LOCATION: (12)..(12)
<223> OTHER INFORMATION: Xaa represents E, M, N, P, T, Q, S, Y, G, D, W,
      R, H or A
<220> FEATURE:
<221> NAME/KEY: MISC_FEATURE
<222> LOCATION: (13)..(13)
<223> OTHER INFORMATION: Xaa represents D, G, I, T, A, S, P or V
<220> FEATURE:
<221> NAME/KEY: MISC_FEATURE
<222> LOCATION: (14)..(14)
<223> OTHER INFORMATION: Xaa represents P, S, T, A, K, G, H, F, Q, D, L,
      I, M, R or Y

<400> SEQUENCE: 21

```
Cys Xaa Asn Tyr Trp Asn Pro Cys Xaa Leu Xaa Xaa Xaa Xaa Cys
1               5                   10                  15
```

<210> SEQ ID NO 22
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents K or R
<220> FEATURE:
<221> NAME/KEY: MISC_FEATURE
<222> LOCATION: (9)..(9)
<223> OTHER INFORMATION: Xaa represents D or T
<220> FEATURE:
<221> NAME/KEY: MISC_FEATURE
<222> LOCATION: (11)..(11)
<223> OTHER INFORMATION: Xaa represents I or V
<220> FEATURE:
<221> NAME/KEY: MISC_FEATURE
<222> LOCATION: (12)..(12)
<223> OTHER INFORMATION: Xaa represents E, M, N, P or T
<220> FEATURE:
<221> NAME/KEY: MISC_FEATURE
<222> LOCATION: (13)..(13)
<223> OTHER INFORMATION: Xaa represents D, G, I or T
<220> FEATURE:
<221> NAME/KEY: MISC_FEATURE
<222> LOCATION: (14)..(14)
<223> OTHER INFORMATION: Xaa represents P, S or T

<400> SEQUENCE: 22

```
Cys Xaa Asn Tyr Trp Asn Pro Cys Xaa Leu Xaa Xaa Xaa Xaa Cys
1               5                   10                  15
```

<210> SEQ ID NO 23
<211> LENGTH: 15
<212> TYPE: PRT
<213> ORGANISM: Artificial
<220> FEATURE:
<223> OTHER INFORMATION: Synthetic peptide ligand

<400> SEQUENCE: 23

```
Cys Lys Asn Tyr Trp Asn Pro Cys Asp Leu Val Thr Ile Ser Cys
1               5                   10                  15
```

<210> SEQ ID NO 24
<211> LENGTH: 15
<212> TYPE: PRT
<213> ORGANISM: Artificial
<220> FEATURE:
<223> OTHER INFORMATION: Synthetic peptide ligand

<400> SEQUENCE: 24

```
Cys Lys Asn Tyr Trp Asn Pro Cys Asp Leu Ile Glu Thr Thr Cys
1               5                   10                  15
```

<210> SEQ ID NO 25
<211> LENGTH: 15
<212> TYPE: PRT
<213> ORGANISM: Artificial
<220> FEATURE:
<223> OTHER INFORMATION: Synthetic peptide ligand

<400> SEQUENCE: 25

```
Cys Lys Asn Tyr Trp Asn Pro Cys Asp Leu Ile Pro Gly Pro Cys
1               5                   10                  15
```

<210> SEQ ID NO 26
<211> LENGTH: 15
<212> TYPE: PRT
<213> ORGANISM: Artificial
<220> FEATURE:
<223> OTHER INFORMATION: Synthetic peptide ligand

<400> SEQUENCE: 26

Cys Lys Asn Tyr Trp Asn Pro Cys Asp Leu Val Met Asp Thr Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic peptide ligand

<400> SEQUENCE: 27

Cys Lys Asn Tyr Trp Asn Pro Cys Asp Leu Ile Gln Asp Ala Cys
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic peptide ligand

<400> SEQUENCE: 28

Cys Lys Asn Tyr Trp Asn Pro Cys Asp Leu Ile Ser Ile Lys Cys
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic peptide ligand

<400> SEQUENCE: 29

Cys Lys Asn Tyr Trp Asn Pro Cys Asp Leu Ile Pro Thr Gly Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic peptide ligand

<400> SEQUENCE: 30

Cys Lys Asn Tyr Trp Asn Pro Cys Asp Leu Val Gln Ile His Cys
1               5                   10                  15

<210> SEQ ID NO 31
<211> LENGTH: 15
<212> TYPE: PRT
<213> ORGANISM: Artificial
<220> FEATURE:
<223> OTHER INFORMATION: Synthetic peptide ligand

<400> SEQUENCE: 31

Cys Lys Asn Tyr Trp Asn Pro Cys Asp Leu Ile Gly Ile Thr Cys
1               5                   10                  15

```
<210> SEQ ID NO 32
<211> LENGTH: 15
<212> TYPE: PRT
<213> ORGANISM: Artificial
<220> FEATURE:
<223> OTHER INFORMATION: Synthetic peptide ligand

<400> SEQUENCE: 32

Cys Lys Asn Tyr Trp Asn Pro Cys Asp Leu Val Asp Thr Phe Cys
1               5                   10                  15

<210> SEQ ID NO 33
<211> LENGTH: 15
<212> TYPE: PRT
<213> ORGANISM: Artificial
<220> FEATURE:
<223> OTHER INFORMATION: Synthetic peptide ligand

<400> SEQUENCE: 33

Cys Lys Asn Tyr Trp Asn Pro Cys Asp Leu Val Glu Ala Gln Cys
1               5                   10                  15

<210> SEQ ID NO 34
<211> LENGTH: 15
<212> TYPE: PRT
<213> ORGANISM: Artificial
<220> FEATURE:
<223> OTHER INFORMATION: Synthetic peptide ligand

<400> SEQUENCE: 34

Cys Lys Asn Phe Trp Asn Pro Cys Asp Leu Ile Pro Ile Ser Cys
1               5                   10                  15

<210> SEQ ID NO 35
<211> LENGTH: 15
<212> TYPE: PRT
<213> ORGANISM: Artificial
<220> FEATURE:
<223> OTHER INFORMATION: Synthetic peptide ligand

<400> SEQUENCE: 35

Cys Lys Asn Tyr Trp Asn Pro Cys Asp Leu Ile Trp Thr Asp Cys
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic peptide ligand

<400> SEQUENCE: 36

Cys Lys Asn Tyr Trp Asn Pro Cys Asp Leu Ile Pro Asp Leu Cys
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic peptide ligand

<400> SEQUENCE: 37

Cys Lys Asn Tyr Trp Asn Pro Cys Asp Leu Leu Glu Ser Thr Cys
1               5                   10                  15

<210> SEQ ID NO 38
```

```
<211> LENGTH: 15
<212> TYPE: PRT
<213> ORGANISM: Artificial
<220> FEATURE:
<223> OTHER INFORMATION: Synthetic peptide ligand

<400> SEQUENCE: 38

Cys Lys Asn Tyr Trp Asn Pro Cys Asp Leu Ile Arg Pro Pro Cys
1               5                   10                  15

<210> SEQ ID NO 39
<211> LENGTH: 15
<212> TYPE: PRT
<213> ORGANISM: Artificial
<220> FEATURE:
<223> OTHER INFORMATION: Synthetic peptide ligand

<400> SEQUENCE: 39

Cys Lys Asn Tyr Trp Asn Pro Cys Asp Leu Leu Gly Ile Ala Cys
1               5                   10                  15

<210> SEQ ID NO 40
<211> LENGTH: 15
<212> TYPE: PRT
<213> ORGANISM: Artificial
<220> FEATURE:
<223> OTHER INFORMATION: Synthetic peptide ligand

<400> SEQUENCE: 40

Cys Lys Asn Tyr Trp Asn Pro Cys Asp Leu Val His Asp Ile Cys
1               5                   10                  15

<210> SEQ ID NO 41
<211> LENGTH: 15
<212> TYPE: PRT
<213> ORGANISM: Artificial
<220> FEATURE:
<223> OTHER INFORMATION: Synthetic peptide ligand

<400> SEQUENCE: 41

Cys Lys Asn Tyr Trp Asn Pro Cys Asp Leu Ile Pro Asp Met Cys
1               5                   10                  15

<210> SEQ ID NO 42
<211> LENGTH: 15
<212> TYPE: PRT
<213> ORGANISM: Artificial
<220> FEATURE:
<223> OTHER INFORMATION: Synthetic peptide ligand

<400> SEQUENCE: 42

Cys Lys Asn Tyr Trp Asn Pro Cys Asp Leu Ile Ala Asp Leu Cys
1               5                   10                  15

<210> SEQ ID NO 43
<211> LENGTH: 15
<212> TYPE: PRT
<213> ORGANISM: Artificial
<220> FEATURE:
<223> OTHER INFORMATION: Synthetic peptide ligand

<400> SEQUENCE: 43

Cys Lys Asn Tyr Trp Asn Pro Cys Asp Leu Leu His Val Arg Cys
1               5                   10                  15

<210> SEQ ID NO 44
<211> LENGTH: 15
```

```
<212> TYPE: PRT
<213> ORGANISM: Artificial
<220> FEATURE:
<223> OTHER INFORMATION: Synthetic peptide ligand

<400> SEQUENCE: 44

Cys Lys Asn Tyr Trp Asn Pro Cys Asp Leu Ile Ala Pro Tyr Cys
1               5                   10                  15

<210> SEQ ID NO 45
<211> LENGTH: 15
<212> TYPE: PRT
<213> ORGANISM: Artificial
<220> FEATURE:
<223> OTHER INFORMATION: Synthetic peptide ligand

<400> SEQUENCE: 45

Cys Lys Asn Tyr Trp Asn Pro Cys Gly Leu Val Tyr Ser Thr Cys
1               5                   10                  15

<210> SEQ ID NO 46
<211> LENGTH: 15
<212> TYPE: PRT
<213> ORGANISM: Artificial
<220> FEATURE:
<223> OTHER INFORMATION: Synthetic peptide ligand

<400> SEQUENCE: 46

Cys Lys Asn Tyr Trp Asn Pro Cys Asp Leu Leu Pro Asp Leu Cys
1               5                   10                  15

<210> SEQ ID NO 47
<211> LENGTH: 15
<212> TYPE: PRT
<213> ORGANISM: Artificial
<220> FEATURE:
<223> OTHER INFORMATION: Synthetic peptide ligand

<400> SEQUENCE: 47

Cys Arg Asn Tyr Trp Asn Pro Cys Thr Leu Ile Asn Ile Thr Cys
1               5                   10                  15

<210> SEQ ID NO 48
<211> LENGTH: 6
<212> TYPE: PRT
<213> ORGANISM: Artificial
<220> FEATURE:
<223> OTHER INFORMATION: Synthetic peptide ligand

<400> SEQUENCE: 48

Gln Lys Phe Glu Ser Arg
1               5

<210> SEQ ID NO 49
<211> LENGTH: 15
<212> TYPE: PRT
<213> ORGANISM: Artificial
<220> FEATURE:
<223> OTHER INFORMATION: Synthetic peptide ligand

<400> SEQUENCE: 49

Cys Gln Lys Phe Glu Ser Arg Cys Arg Val Asp Thr Arg Tyr Cys
1               5                   10                  15

<210> SEQ ID NO 50
<211> LENGTH: 5
<212> TYPE: PRT
```

```
<213> ORGANISM: Artificial
<220> FEATURE:
<223> OTHER INFORMATION: Synthetic peptide ligand

<400> SEQUENCE: 50

Pro Tyr Pro Phe Arg
1               5

<210> SEQ ID NO 51
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents either no amino acid residue or
      a N residue
<220> FEATURE:
<221> NAME/KEY: MISC_FEATURE
<222> LOCATION: (3)..(3)
<223> OTHER INFORMATION: Xaa represents a polar, uncharged amino acid
      residue selected from N, C, Q, M, S and T
<220> FEATURE:
<221> NAME/KEY: MISC_FEATURE
<222> LOCATION: (6)..(6)
<223> OTHER INFORMATION: Xaa represents a non-polar aromatic amino acid
      residue selected from F, W and Y

<400> SEQUENCE: 51

Cys Xaa Xaa Phe Pro Xaa Arg Cys Val Tyr Tyr Pro Asp Ile Cys
1               5                   10                  15

<210> SEQ ID NO 52
<211> LENGTH: 13
<212> TYPE: PRT
<213> ORGANISM: Artificial
<220> FEATURE:
<223> OTHER INFORMATION: Synthetic peptide ligand

<400> SEQUENCE: 52

Cys Pro Tyr Pro Phe Arg Cys Leu His Glu Asn Leu Cys
1               5                   10

<210> SEQ ID NO 53
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(2)
<223> OTHER INFORMATION: Xaa represents either no amino acid residue or
      a N residue
<220> FEATURE:
<221> NAME/KEY: MISC_FEATURE
<222> LOCATION: (3)..(3)
<223> OTHER INFORMATION: Xaa represents N or S
<220> FEATURE:
<221> NAME/KEY: MISC_FEATURE
<222> LOCATION: (6)..(6)
<223> OTHER INFORMATION: Xaa represents F or Y

<400> SEQUENCE: 53

Cys Xaa Xaa Phe Pro Xaa Arg Cys Val Tyr Tyr Pro Asp Ile Cys
1               5                   10                  15

<210> SEQ ID NO 54
<211> LENGTH: 15
```

```
<212> TYPE: PRT
<213> ORGANISM: Artificial
<220> FEATURE:
<223> OTHER INFORMATION: Synthetic peptide ligand

<400> SEQUENCE: 54

Cys Asn Asn Phe Pro Phe Arg Cys Val Tyr Tyr Pro Asp Ile Cys
1               5                   10                  15

<210> SEQ ID NO 55
<211> LENGTH: 14
<212> TYPE: PRT
<213> ORGANISM: Artificial
<220> FEATURE:
<223> OTHER INFORMATION: Synthetic peptide ligand

<400> SEQUENCE: 55

Cys Ser Phe Pro Tyr Arg Cys Val Tyr Tyr Pro Asp Ile Cys
1               5                   10

<210> SEQ ID NO 56
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (6)..(6)
<223> OTHER INFORMATION: Xaa represents a L-homoarginine residue

<400> SEQUENCE: 56

Cys Ser Phe Pro Tyr Xaa Cys Val Tyr Tyr Pro Asp Ile Cys
1               5                   10

<210> SEQ ID NO 57
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(4)
<223> OTHER INFORMATION: Xaa represents a L-azetidine carboxylic acid
      residue

<400> SEQUENCE: 57

Cys Ser Phe Xaa Tyr Arg Cys Val Tyr Tyr Pro Asp Ile Cys
1               5                   10

<210> SEQ ID NO 58
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(4)
<223> OTHER INFORMATION: Xaa represents a L-azetidine carboxylic acid
      residue
<220> FEATURE:
<221> NAME/KEY: MISC_FEATURE
<222> LOCATION: (6)..(6)
<223> OTHER INFORMATION: Xaa represents a L-homoarginine residue

<400> SEQUENCE: 58

Cys Ser Phe Xaa Tyr Xaa Cys Val Tyr Tyr Pro Asp Ile Cys
1               5                   10
```

```
<210> SEQ ID NO 59
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (6)..(6)
<223> OTHER INFORMATION: Xaa respresents an N-alpha-methyl arginine
      residue

<400> SEQUENCE: 59

Cys Ser Phe Pro Tyr Xaa Cys Val Tyr Tyr Pro Asp Ile Cys
1               5                   10

<210> SEQ ID NO 60
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(4)
<223> OTHER INFORMATION: Xaa represents a L-azetidine carboxylic acid
      residue
<220> FEATURE:
<221> NAME/KEY: MISC_FEATURE
<222> LOCATION: (6)..(6)
<223> OTHER INFORMATION: Xaa represents a N-alpha-methyl arginine
      residue

<400> SEQUENCE: 60

Cys Ser Phe Xaa Tyr Xaa Cys Val Tyr Tyr Pro Asp Ile Cys
1               5                   10

<210> SEQ ID NO 61
<211> LENGTH: 21
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (17)..(19)
<223> OTHER INFORMATION: MeGly
<220> FEATURE:
<221> NAME/KEY: MISC_FEATURE
<222> LOCATION: (20)..(21)
<223> OTHER INFORMATION: Xaa represents a D-arginine residue

<400> SEQUENCE: 61

Cys Asn Thr Trp Asn Pro Trp Cys Pro Trp Asp Ala Pro Leu Cys Ala Gly
1               5                   10                  15

Gly Gly Xaa Xaa
            20

<210> SEQ ID NO 62
<211> LENGTH: 20
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (16)..(18)
<223> OTHER INFORMATION: MeGly
<220> FEATURE:
<221> NAME/KEY: MISC_FEATURE
```

```
<222> LOCATION: (19)..(20)
<223> OTHER INFORMATION: Xaa represents a D-arginine residue

<400> SEQUENCE: 62

Cys Ser Phe Pro Tyr Arg Cys Val Tyr Tyr Pro Asp Ile Cys Ala Gly Gly
1               5                   10                  15

Gly Xaa Xaa
        20

<210> SEQ ID NO 63
<211> LENGTH: 20
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(4)
<223> OTHER INFORMATION: Xaa represents a L-azetidine carboxylic acid
      residue
<220> FEATURE:
<221> NAME/KEY: MISC_FEATURE
<222> LOCATION: (6)..(6)
<223> OTHER INFORMATION: Xaa represents a L-homoarginine residue
<220> FEATURE:
<221> NAME/KEY: MOD_RES
<222> LOCATION: (16)..(18)
<223> OTHER INFORMATION: MeGly
<220> FEATURE:
<221> NAME/KEY: MISC_FEATURE
<222> LOCATION: (19)..(20)
<223> OTHER INFORMATION: Xaa represents a D-arginine residue

<400> SEQUENCE: 63

Cys Ser Phe Xaa Tyr Xaa Cys Val Tyr Tyr Pro Asp Ile Cys Ala Gly Gly
1               5                   10                  15

Gly Xaa Xaa
        20

<210> SEQ ID NO 64
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(4)
<223> OTHER INFORMATION: Xaa represents any amino acid residue
<220> FEATURE:
<221> NAME/KEY: MISC_FEATURE
<222> LOCATION: (11)..(14)
<223> OTHER INFORMATION: Xaa represents any amino acid residue

<400> SEQUENCE: 64

Cys Lys Asn Xaa Trp Asn Pro Cys Asp Leu Xaa Xaa Xaa Xaa Cys
1               5                   10                  15

<210> SEQ ID NO 65
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (9)..(14)
<223> OTHER INFORMATION: Xaa represents any amino acid residue

<400> SEQUENCE: 65
```

Cys Gln Lys Phe Glu Ser Arg Cys Xaa Xaa Xaa Xaa Xaa Xaa Cys
1               5                   10                  15

<210> SEQ ID NO 66
<211> LENGTH: 13
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (5)..(5)
<223> OTHER INFORMATION: Xaa represents any amino acid residue
<220> FEATURE:
<221> NAME/KEY: MISC_FEATURE
<222> LOCATION: (8)..(12)
<223> OTHER INFORMATION: Xaa represents any amino acid residue

<400> SEQUENCE: 66

Cys Pro Tyr Pro Xaa Arg Cys Xaa Xaa Xaa Xaa Xaa Cys
1               5                   10

<210> SEQ ID NO 67
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (3)..(3)
<223> OTHER INFORMATION: Xaa represents any amino acid residue
<220> FEATURE:
<221> NAME/KEY: MISC_FEATURE
<222> LOCATION: (9)..(14)
<223> OTHER INFORMATION: Xaa represents any amino acid residue

<400> SEQUENCE: 67

Cys Asn Xaa Trp Asn Pro Trp Cys Xaa Xaa Xaa Xaa Xaa Xaa Cys
1               5                   10                  15

<210> SEQ ID NO 68
<211> LENGTH: 17
<212> TYPE: PRT
<213> ORGANISM: Artificial
<220> FEATURE:
<223> OTHER INFORMATION: Synthetic peptide ligand

<400> SEQUENCE: 68

Ala Cys Lys Asn Tyr Trp Asn Pro Cys Asp Leu Val Thr Ile Ser Cys
1               5                   10                  15

Ala

<210> SEQ ID NO 69
<211> LENGTH: 17
<212> TYPE: PRT
<213> ORGANISM: Artificial
<220> FEATURE:
<223> OTHER INFORMATION: Synthetic peptide ligand

<400> SEQUENCE: 69

Ala Cys Arg Asn Tyr Trp Asn Pro Cys Thr Leu Ile Asn Ile Thr Cys
1               5                   10                  15

Ala

<210> SEQ ID NO 70
<211> LENGTH: 17
<212> TYPE: PRT

-continued

```
<213> ORGANISM: Artificial
<220> FEATURE:
<223> OTHER INFORMATION: Synthetic peptide ligand

<400> SEQUENCE: 70

Ala Cys Gln Lys Phe Glu Ser Arg Cys Arg Val Asp Thr Arg Tyr Cys
1               5                   10                  15
Ala

<210> SEQ ID NO 71
<211> LENGTH: 17
<212> TYPE: PRT
<213> ORGANISM: Artificial
<220> FEATURE:
<223> OTHER INFORMATION: Synthetic peptide ligand

<400> SEQUENCE: 71

Ala Cys Pro Leu Ser Asp Thr Leu Cys Tyr Arg Arg Met Pro Pro Cys
1               5                   10                  15
Ala

<210> SEQ ID NO 72
<211> LENGTH: 15
<212> TYPE: PRT
<213> ORGANISM: Artificial
<220> FEATURE:
<223> OTHER INFORMATION: Synthetic peptide ligand

<400> SEQUENCE: 72

Ala Cys Pro Tyr Pro Phe Arg Cys Leu His Glu Asn Leu Cys Ala
1               5                   10                  15

<210> SEQ ID NO 73
<211> LENGTH: 17
<212> TYPE: PRT
<213> ORGANISM: Artificial
<220> FEATURE:
<223> OTHER INFORMATION: Synthetic peptide ligand

<400> SEQUENCE: 73

Ala Cys Asn Thr Trp Asn Pro Trp Cys Gly Trp Val Gly Gly Phe Cys
1               5                   10                  15
Ala

<210> SEQ ID NO 74
<211> LENGTH: 17
<212> TYPE: PRT
<213> ORGANISM: Artificial
<220> FEATURE:
<223> OTHER INFORMATION: Synthetic peptide ligand

<400> SEQUENCE: 74

Ala Cys Asn Asn Phe Pro Phe Arg Cys Val Tyr Tyr Pro Asp Ile Cys
1               5                   10                  15
Ala

<210> SEQ ID NO 75
<211> LENGTH: 17
<212> TYPE: PRT
<213> ORGANISM: Artificial
<220> FEATURE:
<223> OTHER INFORMATION: Synthetic peptide ligand

<400> SEQUENCE: 75
```

```
Ala Cys Lys Asn Tyr Trp Asn Pro Cys Asp Leu Ile Glu Thr Thr Cys
1               5                   10                  15

Ala
```

<210> SEQ ID NO 76
<211> LENGTH: 17
<212> TYPE: PRT
<213> ORGANISM: Artificial
<220> FEATURE:
<223> OTHER INFORMATION: Synthetic peptide ligand

<400> SEQUENCE: 76

```
Ala Cys Lys Asn Tyr Trp Asn Pro Cys Asp Leu Ile Pro Gly Pro Cys
1               5                   10                  15

Ala
```

<210> SEQ ID NO 77
<211> LENGTH: 17
<212> TYPE: PRT
<213> ORGANISM: Artificial
<220> FEATURE:
<223> OTHER INFORMATION: Synthetic peptide ligand

<400> SEQUENCE: 77

```
Ala Cys Lys Asn Tyr Trp Asn Pro Cys Asp Leu Val Met Asp Thr Cys
1               5                   10                  15

Ala
```

<210> SEQ ID NO 78
<211> LENGTH: 17
<212> TYPE: PRT
<213> ORGANISM: Artificial
<220> FEATURE:
<223> OTHER INFORMATION: Synthetic peptide ligand

<400> SEQUENCE: 78

```
Ala Cys Asn His Trp Asn Pro Trp Cys Ser Val Glu Pro Pro Val Cys
1               5                   10                  15

Ala
```

<210> SEQ ID NO 79
<211> LENGTH: 17
<212> TYPE: PRT
<213> ORGANISM: Artificial
<220> FEATURE:
<223> OTHER INFORMATION: Synthetic peptide ligand

<400> SEQUENCE: 79

```
Ala Cys Asn Thr Trp Asn Pro Trp Cys Pro Trp Asp Ala Pro Leu Cys
1               5                   10                  15

Ala
```

<210> SEQ ID NO 80
<211> LENGTH: 17
<212> TYPE: PRT
<213> ORGANISM: Artificial
<220> FEATURE:
<223> OTHER INFORMATION: Synthetic peptide ligand

<400> SEQUENCE: 80

```
Ala Cys Asn His Trp Asn Pro Trp Cys Ser Ala Asp Pro Pro Ile Cys
1               5                   10                  15

Ala
```

```
<210> SEQ ID NO 81
<211> LENGTH: 17
<212> TYPE: PRT
<213> ORGANISM: Artificial
<220> FEATURE:
<223> OTHER INFORMATION: Synthetic peptide ligand

<400> SEQUENCE: 81

Ala Cys Asn Tyr Trp Asn Pro Trp Cys Pro Trp Asp Ala Pro Leu Cys
1               5                   10                  15

Ala

<210> SEQ ID NO 82
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION

<400> SEQUENCE: 82

Cys Arg Asn Tyr Trp Asn Pro Cys Thr Leu Ile Asn Ile Thr Cys
1               5                   10                  15

<210> SEQ ID NO 83
<211> LENGTH: 21
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(19)
<223> OTHER INFORMATION: MeGly
<220> FEATURE:
<221> NAME/KEY: MISC_FEATURE
<222> LOCATION: (20)..(21)
<223> OTHER INFORMATION: Xaa represents a D-arginine residue

<400> SEQUENCE: 83

Cys Arg Asn Tyr Trp Asn Pro Cys Thr Leu Ile Asn Ile Thr Cys Ala
1               5                   10                  15

Gly Gly Gly Xaa Xaa
            20

<210> SEQ ID NO 84
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION

<400> SEQUENCE: 84

Cys Asn Thr Trp Asn Pro Trp Cys Pro Trp Asp Ala Pro Leu Cys
1               5                   10                  15
```

```
<210> SEQ ID NO 85
<211> LENGTH: 21
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(19)
<223> OTHER INFORMATION: MeGly
<220> FEATURE:
<221> NAME/KEY: MISC_FEATURE
<222> LOCATION: (20)..(21)
<223> OTHER INFORMATION: Xaa represents a D-arginine residue

<400> SEQUENCE: 85

Cys Asn Thr Trp Asn Pro Trp Cys Pro Trp Asp Ala Pro Leu Cys Ala
1               5                   10                  15

Gly Gly Gly Xaa Xaa
            20

<210> SEQ ID NO 86
<211> LENGTH: 13
<212> TYPE: PRT
<213> ORGANISM: Artificial
<220> FEATURE:
<223> OTHER INFORMATION: Synthetic peptide ligand

<400> SEQUENCE: 86

Cys Ser Trp Pro Ala Arg Cys Leu His Gln Asp Leu Cys
1               5                   10

<210> SEQ ID NO 87
<211> LENGTH: 6
<212> TYPE: PRT
<213> ORGANISM: Artificial
<220> FEATURE:
<223> OTHER INFORMATION: Synthetic peptide ligand

<400> SEQUENCE: 87

Val Tyr Tyr Pro Asp Ile
1               5

<210> SEQ ID NO 88
<211> LENGTH: 5
<212> TYPE: PRT
<213> ORGANISM: Artificial
<220> FEATURE:
<223> OTHER INFORMATION: Synthetic peptide ligand

<400> SEQUENCE: 88

Ser Phe Pro Tyr Arg
1               5

<210> SEQ ID NO 89
<211> LENGTH: 14
<212> TYPE: PRT
<213> ORGANISM: Artificial
<220> FEATURE:
<223> OTHER INFORMATION: Synthetic peptide ligand

<400> SEQUENCE: 89

Cys Ser Trp Pro Ala Arg Cys Val Tyr Tyr Pro Asp Ile Cys
1               5                   10
```

```
<210> SEQ ID NO 90
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION

<400> SEQUENCE: 90

Cys Ser Phe Pro Tyr Arg Cys Val Tyr Tyr Pro Asp Ile Cys
1               5                   10

<210> SEQ ID NO 91
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Xaa represents a L-homoarginine residue

<400> SEQUENCE: 91

Cys Ser Phe Pro Tyr Xaa Cys Val Tyr Tyr Pro Asp Ile Cys
1               5                   10

<210> SEQ ID NO 92
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa represents a L-azetidine carboxylic acid
      residue
<220> FEATURE:
<221> NAME/KEY: MISC_FEATURE
<222> LOCATION: (6)..(6)
<223> OTHER INFORMATION: Xaa represents a L-homoarginine residue

<400> SEQUENCE: 92

Cys Ser Phe Xaa Tyr Xaa Cys Val Tyr Tyr Pro Asp Ile Cys
1               5                   10

<210> SEQ ID NO 93
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Xaa represents a N-alpha-methyl arginine
```

```
                residue

<400> SEQUENCE: 93

Cys Ser Phe Pro Tyr Xaa Cys Val Tyr Tyr Pro Asp Ile Cys
1               5                   10

<210> SEQ ID NO 94
<211> LENGTH: 14
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa represents a L-azetidine carboxylic acid
        residue
<220> FEATURE:
<221> NAME/KEY: MISC_FEATURE
<222> LOCATION: (6)..(6)
<223> OTHER INFORMATION: Xaa represents a N-alpha-methyl arginine
        residue

<400> SEQUENCE: 94

Cys Ser Phe Xaa Tyr Xaa Cys Val Tyr Tyr Pro Asp Ile Cys
1               5                   10

<210> SEQ ID NO 95
<211> LENGTH: 20
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(18)
<223> OTHER INFORMATION: MeGly
<220> FEATURE:
<221> NAME/KEY: MISC_FEATURE
<222> LOCATION: (19)..(20)
<223> OTHER INFORMATION: Xaa represents a D-arginine residue

<400> SEQUENCE: 95

Cys Ser Phe Pro Tyr Arg Cys Val Tyr Tyr Pro Asp Ile Cys Ala Gly
1               5                   10                  15

Gly Gly Xaa Xaa
            20

<210> SEQ ID NO 96
<211> LENGTH: 20
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa represents a L-azetidine carboxylic acid
        residue
<220> FEATURE:
```

```
<221> NAME/KEY: MISC_FEATURE
<222> LOCATION: (6)..(6)
<223> OTHER INFORMATION: Xaa represents a L-homoarginine residue
<220> FEATURE:
<221> NAME/KEY: MOD_RES
<222> LOCATION: (16)..(18)
<223> OTHER INFORMATION: MeGly
<220> FEATURE:
<221> NAME/KEY: MISC_FEATURE
<222> LOCATION: (19)..(20)
<223> OTHER INFORMATION: Xaa represents a D-arginine residue

<400> SEQUENCE: 96

Cys Ser Phe Xaa Tyr Xaa Cys Val Tyr Tyr Pro Asp Ile Cys Ala Gly
1               5                   10                  15

Gly Gly Xaa Xaa
            20

<210> SEQ ID NO 97
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (2)..(7)
<223> OTHER INFORMATION: Xaa represents any amino acid residue
<220> FEATURE:
<221> NAME/KEY: MISC_FEATURE
<222> LOCATION: (9)..(14)
<223> OTHER INFORMATION: Xaa represents any amino acid residue

<400> SEQUENCE: 97

Cys Xaa Xaa Xaa Xaa Xaa Xaa Cys Xaa Xaa Xaa Xaa Xaa Xaa Cys
1               5                   10                  15

<210> SEQ ID NO 98
<211> LENGTH: 5
<212> TYPE: PRT
<213> ORGANISM: Artificial
<220> FEATURE:
<223> OTHER INFORMATION: Synthetic peptide ligand
<220> FEATURE:
<221> NAME/KEY: MOD_RES
<222> LOCATION: (1)..(3)
<223> OTHER INFORMATION: MeGly
<220> FEATURE:
<221> NAME/KEY: MISC_FEATURE
<222> LOCATION: (4)..(5)
<223> OTHER INFORMATION: Xaa represents a D-arginine residue

<400> SEQUENCE: 98

Gly Gly Gly Xaa Xaa
1               5

<210> SEQ ID NO 99
<211> LENGTH: 15
<212> TYPE: PRT
<213> ORGANISM: Artificial
<220> FEATURE:
<223> OTHER INFORMATION: Synthetic peptide ligand
<220> FEATURE:
<221> NAME/KEY: MISC_FEATURE
<222> LOCATION: (4)..(7)
<223> OTHER INFORMATION: Xaa represents any amino acid residue

<400> SEQUENCE: 99

Cys Asn Asn Xaa Xaa Xaa Xaa Cys Val Tyr Tyr Pro Asp Ile Cys
1               5                   10                  15
```

```
<210> SEQ ID NO 100
<211> LENGTH: 4
<212> TYPE: PRT
<213> ORGANISM: Artificial
<220> FEATURE:
<223> OTHER INFORMATION: Synthetic peptide motif

<400> SEQUENCE: 100

Phe Pro Phe Arg
1
```

POLYPEPTIDE LIGANDS SPECIFIC FOR PLASMA KALLIKREIN

FIELD OF THE INVENTION

The present invention relates to polypeptides which are covalently bound to molecular scaffolds such that two or more peptide loops are subtended between attachment points to the scaffold. In particular, the invention describes peptides which are specific for the human and rat protease plasma kallikrein and are modified in one or two peptide loops to enhance potency and/or protease resistance.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)$_6$-Cys-(Xaa)$_6$-Cys) (SEQ ID NO: 97) were displayed on phage and cyclised by covalently linking the cysteine side chains to a small molecule (tris-(bromomethyl)benzene). Bicyclic peptides isolated in affinity selections to the human proteases cathepsin G and plasma kallikrein (PK) demonstrated nanomolar inhibitory constants. WO 2013/050615 and WO 2013/050616 disclose further bicyclic peptide ligands specific for human plasma kallikrein.

SUMMARY OF THE INVENTION

According to a first aspect of the invention, there is provided a peptide ligand specific for plasma kallikrein comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises a peptide sequence selected from any of:

(a)
                              (SEQ ID NO: 1)
-$C_i$-N-X-W-N-P-W-$C_{ii}$-O/U-X-X-X-O/J-X-$C_{iii}$-;

(b)
                              (SEQ ID NO: 2)
-$C_i$-B-N-J-W-N-P-$C_{ii}$-X-L-O-X-X-X-$C_{iii}$-;

(c)
                              (SEQ ID NO: 3)
-$C_i$-Q-K-F-E-S-R-$C_{ii}$-X-X-X-X-X-X-$C_{iii}$-;

(d)
                              (SEQ ID NO: 4)
-$C_i$-P-L-S-D-T-L-$C_{ii}$-Y-R-R-M-P-P-$C_{iii}$-;

(e)
                              (SEQ ID NO: 5)
-$C_i$-P-Y-P-F-R-$C_{ii}$-X-H-X-X-X-$C_{iii}$-;
and (f)
                              (SEQ ID NO: 6)
-$C_i$-(N)$_a$-U-J-P-J-R-$C_{ii}$-V-Y-Y-P-D-I-$C_{iii}$-;

or a modified derivative, or pharmaceutically acceptable salt, thereof;
wherein:
$C_i$, $C_{ii}$ and $C_{iii}$ represent first, second and third cysteine residues, respectively;
subscript "a" represents an integer selected from 0 or 1;
X represents any amino acid residue;
O represents a non-polar aliphatic amino acid residue selected from G, A, I, L, P and V;
J represents a non-polar aromatic amino acid residue selected from F, W and Y;
U represents a polar, uncharged amino acid residue selected from N, C, Q, M, S and T; and
B represents a polar, positively charged amino acid residue selected from R, H and K.

The novel kallikrein binding bicyclic peptide ligands of the invention were identified following biological selections as described herein in the Examples. By switching the target bait between human and rat kallikrein during the biological selections, lead sequences with good cross-reactivity between the species were identified. Solubilising modifications on the molecules were introduced in order to enhance the ability to formulate the bicyclic peptide leads, and rat pharmacokinetic analyses revealed sequences with high metabolic stability in vivo.

According to a further aspect of the invention, there is provided a pharmaceutical composition comprising a peptide ligand as defined herein in combination with one or more pharmaceutically acceptable excipients.

According to a further aspect of the invention, there is provided a peptide ligand as defined herein for use in preventing, suppressing or treating inflammatory states, allergic hypersensitivity, cancer, bacterial or viral infection, and autoimmune disorders

DETAILED DESCRIPTION OF THE INVENTION

Figure 1:
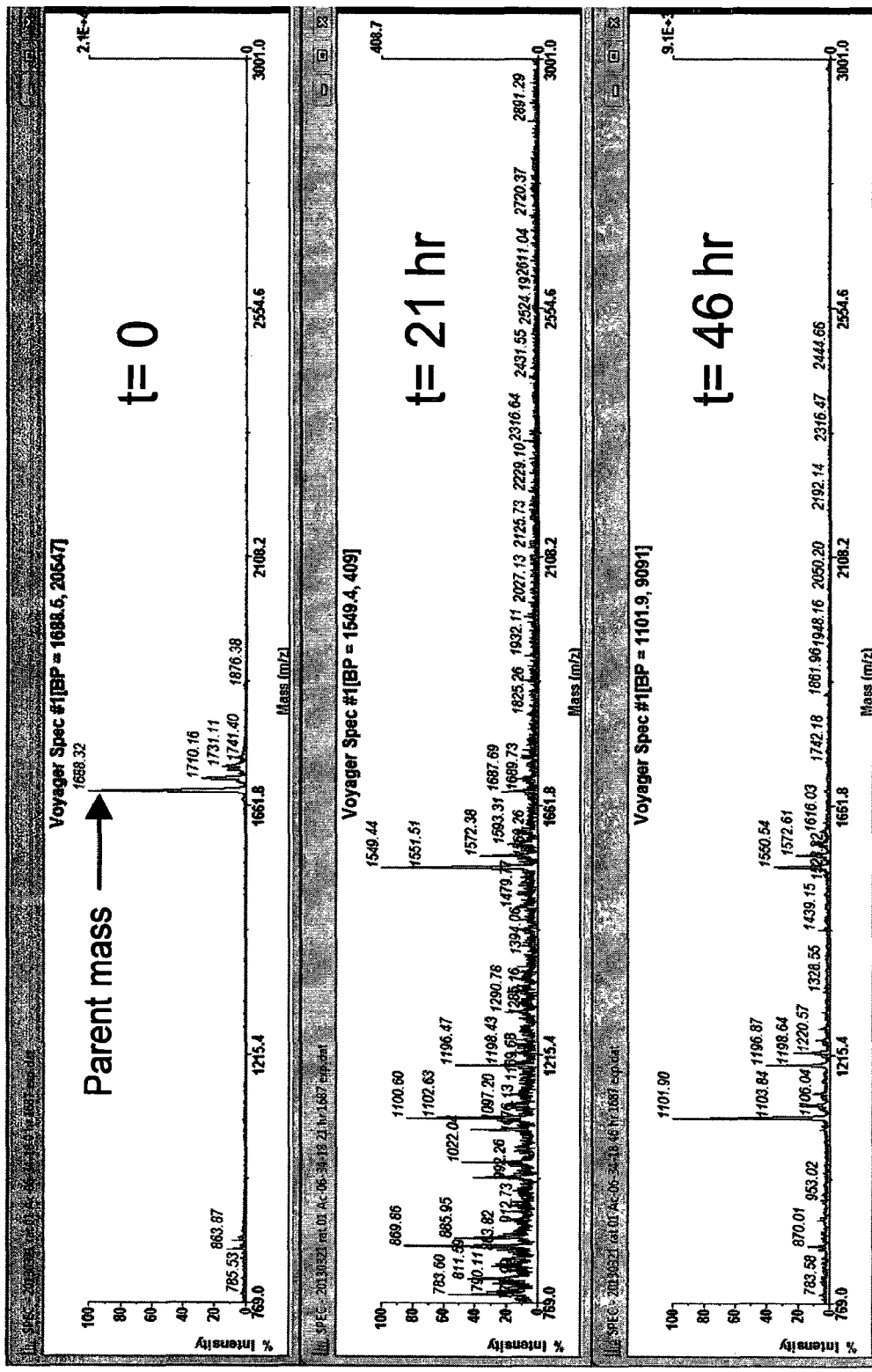
FIG. 1: Comparative rat plasma stability of the 06-34-18 control against the cross-reactive novel kallikrein-binding bicycle leads.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

In one embodiment, the peptide ligand comprises the sequence of formula (a). The consensus sequence of formula (a) contains motifs from both the initial lead bicycle peptide 06-259 as well as each of the most promising peptide sequences identified by affinity maturation of the initial lead as described in Example 1 and Tables 2 and 4.

In a further embodiment, the peptide of formula (a) comprises a sequence selected from -$C_i$-N-X-W-N-P-W-$C_{ii}$-O/U-X-X-X-O-X-$C_{ii}$- (SEQ ID NO: 7).

In a yet further embodiment, the peptide of formula (a) comprises a sequence selected from (SEQ ID NO: 8)
-$C_i$-N-T/H/Y-W-N-P-W-$C_{ii}$-G/S/P-A/V/W/D/S-D/E/V/T/P-

A/G/P/I/R/D-G/P/Y/I-F/I/L/V/R/G/D-$C_{iii}$-.

In a yet further embodiment, the peptide of formula (a) comprises a sequence selected from (SEQ ID NO: 9)
-$C_i$-N-T/H/Y-W-N-P-W-$C_{ii}$-G/S/P-A/V/W-D/E/V-A/G/P-

G/P-F/I/L/V-$C_{iii}$-.

In a yet further embodiment, the peptide of formula (a) comprises a sequence selected from:

(SEQ ID NO: 10)
-$C_i$-N-T-W-N-P-W-$C_{ii}$-G-W-V-G-G-F-$C_{iii}$-(06-259);

(SEQ ID NO: 11)
-$C_i$-N-H-W-N-P-W-$C_{ii}$-S-V-E-P-P-V-$C_{iii}$-(06-259-01);

(SEQ ID NO: 12)
-$C_i$-N-T-W-N-P-W-$C_{ii}$-P-W-D-A-P-L-$C_{iii}$-(06-259-02);

(SEQ ID NO: 13)
-$C_i$-N-H-W-N-P-W-$C_{ii}$-S-A-D-P-P-I-$C_{iii}$-(06-259-03);

(SEQ ID NO: 14)
-$C_i$-N-Y-W-N-P-W-$C_{ii}$-P-W-D-A-P-L-$C_{iii}$-(06-259-04);

(SEQ ID NO: 15)
-$C_i$-N-H-W-N-P-W-$C_{ii}$-S-A-D-P-P-R-$C_{iii}$-(06-259-F1);

(SEQ ID NO: 16)
-$C_i$-N-H-W-N-P-W-$C_{ii}$-P-A-D-I-P-V-$C_{iii}$-(06-259-E2);

(SEQ ID NO: 17)
-$C_i$-N-H-W-N-P-W-$C_{ii}$-S-D-D-P-Y-I-$C_{iii}$-(06-259-H3);

(SEQ ID NO: 18)
-$C_i$-N-H-W-N-P-W-$C_{ii}$-S-S-D-P-P-V-$C_{iii}$-(06-259-H4)

(SEQ ID NO: 19)
-$C_i$-N-Y-W-N-P-W-$C_{ii}$-S-D-T-R-I-G-$C_{iii}$-(06-259-A6);
and (SEQ ID NO: 20)
-$C_i$-N-T-W-N-P-W-$C_{ii}$-S-W-P-D-I-D-$C_{iii}$-(06-259-F2).

In a still yet further embodiment, the peptide of formula (a) comprises a sequence selected from:

(SEQ ID NO: 11)
-$C_i$-N-H-W-N-P-W-$C_{ii}$-S-V-E-P-P-V-$C_{iii}$-(06-259-01);

(SEQ ID NO: 12)
-$C_i$-N-T-W-N-P-W-$C_{ii}$-P-W-D-A-P-L-$C_{iii}$-(06-259-02);

(SEQ ID NO: 13)
-$C_i$-N-H-W-N-P-W-$C_{ii}$-S-A-D-P-P-I-$C_{iii}$-(06-259-03);

and (SEQ ID NO: 14)
-$C_i$-N-Y-W-N-P-W-$C_{ii}$-P-W-D-A-P-L-$C_{iii}$- (06-259-04).

The peptides of this embodiment were identified to be one of the most potent candidates following affinity maturation (see Example 1 and Table 4). Furthermore, each of the peptides of this embodiment were identified to demonstrate both high potencies and good cross-reactivity between rat and human kallikrein (see Table 5).

In a still yet further embodiment, the peptide of formula (a) comprises a sequence selected from -$C_i$-N-T-W-N-P-W-$C_{ii}$-P-W-D-A-P-L-$C_{iii}$- (06-259-02) (SEQ ID NO: 12). The peptide of this embodiment was identified to be the most potent, cross-reactive and stable member of the family of peptide ligands within formula (a) (see Examples 1 and 2). For example, initial screening using Method #1 described herein indicated 06-259-02 to be more stable than most of the remaining bicycle leads, as judged by a window of detection of up to 10 days (data not shown). Moreover, the ex vivo stability was also reproducible in vivo, specifically in the rat, where metabolism of the peptide was virtually absent as judged by the clearance and comparison with the known glomerular filtration rate (Example 4).

In one embodiment, the peptide ligand comprises the sequence of formula (b). The consensus sequence of formula (b) contains motifs from both the initial lead bicycle peptides 06-254 and 06-255 as well as each of the most promising peptide sequences identified by affinity maturation of the initial lead 06-254 as described in Example 1 and Tables 2 and 3.

In a further embodiment, the peptide of formula (b) comprises a sequence selected from -$C_i$-K/R-N-Y-W-N-P-$C_{ii}$-D/T/G-L-I/V/L-E/M/N/P/T/Q/S/Y/G/D/W/R/H/A-D/G/I/T/NS/P/V-P/S/T/A/K/G/H/F/Q/D/L/I/M/R/Y-$C_{iii}$- (SEQ ID NO: 21).

In a yet further embodiment, the peptide of formula (b) comprises a sequence selected from (SEQ ID NO: 22)
-$C_i$-K/R-N-Y-W-N-P-$C_{ii}$-D/T-L-I/V-E/M/N/P/T-D/G/I/T-P/S/T-$C_{iii}$-.

In a further embodiment, the peptide of formula (b) comprises a sequence selected from:

(SEQ ID NO: 23)
-$C_i$-K-N-Y-W-N-P-$C_{ii}$-D-L-V-T-I-S-$C_{iii}$- (06-254);

(SEQ ID NO: 24)
-$C_i$-K-N-Y-W-N-P-$C_{ii}$-D-L-I-E-T-T-$C_{iii}$- (06-254-01);

(SEQ ID NO: 25)
-$C_i$-K-N-Y-W-N-P-$C_{ii}$-D-L-I-P-G-P-$C_{iii}$- (06-254-02);

(SEQ ID NO: 26)
-$C_i$-K-N-Y-W-N-P-$C_{ii}$-D-L-V-M-D-T-$C_{iii}$- (06-254-03);

(SEQ ID NO: 27)
-$C_i$-K-N-Y-W-N-P-$C_{ii}$-D-L-I-Q-D-A-$C_{iii}$- (06-254-F4);

(SEQ ID NO: 28)
-$C_i$-K-N-Y-W-N-P-$C_{ii}$-D-L-I-S-I-K-$C_{iii}$- (06-254-B3);

(SEQ ID NO: 29)
-$C_i$-K-N-Y-W-N-P-$C_{ii}$-D-L-I-P-T-G-$C_{iii}$- (06-254-G3);

(SEQ ID NO: 30)
-$C_i$-K-N-Y-W-N-P-$C_{ii}$-D-L-V-Q-I-H-$C_{iii}$- (06-254-H4);

(SEQ ID NO: 31)
-$C_i$-K-N-Y-W-N-P-$C_{ii}$-D-L-I-G-I-T-$C_{iii}$- (06-254-G2);

(SEQ ID NO: 32)
-$C_i$-K-N-Y-W-N-P-$C_{ii}$-D-L-V-D-T-F-$C_{iii}$- (06-254-A4);

(SEQ ID NO: 33)
-$C_i$-K-N-Y-W-N-P-$C_{ii}$-D-L-V-E-A-Q-$C_{iii}$- (06-254-G4);

(SEQ ID NO: 34)
-$C_i$-K-N-F-W-N-P-$C_{ii}$-D-L-I-P-I-S-$C_{iii}$- (06-254-D3);

(SEQ ID NO: 35)
-$C_i$-K-N-Y-W-N-P-$C_{ii}$-D-L-I-W-T-D-$C_{iii}$- (06-254-E2);

(SEQ ID NO: 36)
-$C_i$-K-N-Y-W-N-P-$C_{ii}$-D-L-I-P-D-L-$C_{iii}$- (06-254-F5);

(SEQ ID NO: 37)
-$C_i$-K-N-Y-W-N-P-$C_{ii}$-D-L-L-E-S-T-$C_{iii}$- (06-254-E5);

(SEQ ID NO: 38)
-$C_i$-K-N-Y-W-N-P-$C_{ii}$-D-L-I-R-P-P-$C_{iii}$- (06-254-D1);

(SEQ ID NO: 39)
-$C_i$-K-N-Y-W-N-P-$C_{ii}$-D-L-L-G-I-A-$C_{iii}$- (06-254-B9);

(SEQ ID NO: 40)
-$C_i$-K-N-Y-W-N-P-$C_{ii}$-D-L-V-H-D-I-$C_{iii}$- (06-254-E3);

(SEQ ID NO: 41)
-$C_i$-K-N-Y-W-N-P-$C_{ii}$-D-L-I-P-D-M-$C_{iii}$- (06-254-D6);

(SEQ ID NO: 42)
-$C_i$-K-N-Y-W-N-P-$C_{ii}$-D-L-I-A-D-L-$C_{iii}$- (06-254-H3);

(SEQ ID NO: 43)
-$C_i$-K-N-Y-W-N-P-$C_{ii}$-D-L-L-H-V-R-$C_{iii}$- (06-254-A7);

(SEQ ID NO: 44)
-$C_i$-K-N-Y-W-N-P-$C_{ii}$-D-L-I-A-P-Y-$C_{iii}$- (06-254-C1);

(SEQ ID NO: 45)
-$C_i$-K-N-Y-W-N-P-$C_{ii}$-G-L-V-Y-S-T-$C_{iii}$- (06-254-E6);

(SEQ ID NO: 46)
-$C_i$-K-N-Y-W-N-P-$C_{ii}$-D-L-L-P-D-L-$C_{iii}$- (06-254-B1);
and (SEQ ID NO: 47)
-$C_i$-R-N-Y-W-N-P-$C_{ii}$-T-L-I-N-I-T-$C_{iii}$- (06-255).

In a still yet further embodiment, the peptide of formula (b) comprises a sequence selected from:

(SEQ ID NO: 24)
-$C_i$-K-N-Y-W-N-P-$C_{ii}$-D-L-I-E-T-T-$C_{iii}$- (06-254-01);

(SEQ ID NO: 25)
-$C_i$-K-N-Y-W-N-P-$C_{ii}$-D-L-I-P-G-P-$C_{iii}$- (06-254-02);

(SEQ ID NO: 26)
-$C_i$-K-N-Y-W-N-P-$C_{ii}$-D-L-V-M-D-T-$C_{iii}$- (06-254-03);
and (SEQ ID NO: 47)
-$C_i$-R-N-Y-W-N-P-$C_{ii}$-T-L-I-N-I-T-$C_{iii}$- (06-255).

The peptides of this embodiment were identified to be the most potent candidates following affinity maturation (see Example 1 and Table 3). Furthermore, each of the peptides of this embodiment were identified to demonstrate both high potencies and good cross-reactivity between rat and human kallikrein (see Table 5).

In a still yet further embodiment, the peptide of formula (b) comprises a sequence selected from:

-C$_i$-K-N-Y-W-N-P-C$_{ii}$-D-L-I-P-G-P-C$_{iii}$- (06-254-02); (SEQ ID NO: 25)
and -C$_i$-R-N-Y-W-N-P-C$_{ii}$-T-L-I-N-I-T-C$_{iii}$- (06-255). (SEQ ID NO: 47)

The peptides of this embodiment were identified to be the most potent member of each family of peptide ligands within formula (b) (see Example 2).

In a still yet further embodiment, the peptide of formula (b) comprises a sequence selected from -C$_i$-R-N-Y-W-N-P-C$_{ii}$-T-L-I-N-I-T-C$_{iii}$- (06-255) (SEQ ID NO: 47). Initial screening using Method #1 described herein indicated 06-255 to be more stable than most of the remaining bicycle leads, as judged by a window of detection of up to 10 days (data not shown).

In one embodiment, the peptide ligand comprises the sequence of formula (c). The consensus sequence of formula (c) contains the fixed QKFESR (SEQ ID NO: 48) motif in loop 1 from the initial lead bicycle peptide 06-256 and similar derivatives contained therein, as described in Example 1 and Table 2.

In a further embodiment, the peptide of formula (c) comprises a sequence selected from -C$_i$-Q-K-F-E-S-R-C$_{ii}$-R-V-D-T-R-Y-C$_{iii}$- (06-256) (SEQ ID NO: 49). The cross-reactivity data for 06-256 between human, rat and rabbit is shown in Tables 1 and 5.

In one embodiment, the peptide ligand comprises the sequence of formula (d). The peptide sequence of formula (d) corresponds to the sequence of initial lead bicycle peptide 06-257 as described in Example 1 and Table 1. The cross-reactivity data for 06-257 between human, rat and rabbit is shown in Tables 1 and 5.

In one embodiment, the peptide ligand comprises the sequence of formula (e). The consensus sequence of formula (e) contains the conserved PYPFR (SEQ ID NO: 50) motif in loop 1 and a histidine residue at position 2 in loop 2 in the initial lead bicycle peptide 06-258 where the consensus is based on similar sequences identified during the initial selection rounds (Example 1 and Table 2).

In a further embodiment, the peptide of formula (f) comprises a sequence selected from -C$_i$-(N)$_a$-U-F-P-J-R-C$_{ii}$-V-Y-Y-P-D-I-C$_{iii}$- (SEQ ID NO: 51).

In a further embodiment, the peptide of formula (e) comprises a sequence selected from -C$_i$-P-Y-P-F-R-C$_{ii}$-L-H-E-N-L-C$_{iii}$- (06-258) (SEQ ID NO: 52). The peptide of this embodiment was identified to demonstrate both high potency and good cross-reactivity between rat and human kallikrein (see Table 5).

In one embodiment, the peptide ligand comprises the sequence of formula (f). The consensus sequence of formula (f) contains motifs from both the initial lead bicycle peptides 06-261 and 06-550 as well as each of the most promising peptide sequences identified from the initial screening as described in Example 1 and Tables 1 and 2.

In a yet further embodiment, the peptide of formula (f) comprises a sequence selected from -C$_i$-(N)$_a$-N/S-F-P-F/Y-R-C$_{ii}$-V-Y-Y-P-D-I-C$_{iii}$- (SEQ ID NO: 53).

In a further embodiment, the peptide of formula (f) comprises a sequence selected from:

-C$_i$-N-N-F-P-F-R-C$_{ii}$-V-Y-Y-P-D-I-C$_{iii}$- (06-261); (SEQ ID NO: 54)
or

-C$_i$-S-F-P-Y-R-C$_{ii}$-V-Y-Y-P-D-I-C$_{iii}$- (06-550). (SEQ ID NO: 55)

In a still yet further embodiment, the peptide of formula (f) comprises a sequence selected from -C$_i$-N-N-F-P-F-R-C$_{ii}$-V-Y-Y-P-D-I-C$_{iii}$- (06-261) (SEQ ID NO: 54). The peptide of this embodiment was identified to be one of the most potent candidates following selections (see Example 1 and Table 1). Furthermore, the peptide of this embodiment was identified to demonstrate both high potency and good cross-reactivity between rat and human kallikrein (see Table 5).

In an alternative embodiment, the peptide of formula (f) comprises a sequence selected from -C$_i$-S-F-P-Y-R-C$_{ii}$-V-Y-Y-P-D-I-C$_{iii}$- (06-550) (SEQ ID NO: 55). Data demonstrating the advantages of 06-550 is described in Examples 3 and 4 wherein it can be seen to be a potent chimeric bicycle. In particular, the cross-reactivity between human, rat and rabbit kallikrein can be seen in Table 7.

In one embodiment, certain peptide ligands of the invention are specific for human, rat and/or rabbit plasma kallikrein. In a further embodiment, certain peptide ligands of the invention are specific for human and/or rat plasma kallikrein. In a yet further embodiment, certain peptide ligands of the invention are specific for human plasma kallikrein.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide lead candidate peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states.

Pharmaceutically Acceptable Salts

It will be appreciated that salt forms are within the scope of this invention, and references to compounds of the formula (I) include the salt forms of said compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more hydrophobic amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the α-carbon of one or more amino acid residues with another chemical group, and post-synthetic modification of amino acids such as cysteine, lysine, glutamate/aspartate and tyrosine with suitable amine, thiol, carboxylic acid and phenol-reactive reagents.

In one embodiment, the modified derivative comprises an N-terminal and/or C-terminal modification.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidase and avoids the potential for degradation of the bicyclic peptide.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and avoids the potential for degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are no more recognised by degradative proteases nor have any effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In a further embodiment, a proline residue may be replaced with an L-azetidine carboxylic acid residue and/or an arginine residue may be replaced with an N-α-methyl arginine or L-homoarginine residue. Data is presented herein which demonstrates that the presence of such non-natural amino acids enhances proteolytic stability and while maintaining or enhancing target affinity of the bicyclic peptide ligands.

Example 3 demonstrates selected non-natural derivatives of the 06-550 peptide ligand. Thus, in one embodiment, the invention provides a non-natural derivative of formula (f) which comprises a peptide having a sequence selected from:

```
                                                (SEQ ID NO: 56)
-C_i-S-F-P-Y-[hR]-C_ii-V-Y-Y-P-D-I-C_iii- ((06-550)

HArg5);

(SEQ ID NO: 57)
-C_i-S-F-[Aze]-Y-R-C_ii-V-Y-Y-P-D-I-C_iii-;

(SEQ ID NO: 58)
-C_i-S-F-[Aze]-Y-[hR]-C_ii-V-Y-Y-P-D-I-C_iii- ((06-550) Aze3 HArg5);

(SEQ ID NO: 59)
-C_i-S-F-P-Y-[NMeR]-C_ii-V-Y-Y-P-D-I-C_iii- ((06-550) NMeArg5);
and
```

-continued (SEQ ID NO: 60)
-C$_i$-S-F-[Aze]-Y-[NMeR]-C$_{ii}$-V-Y-Y-P-D-I-C$_{iii}$-

((06-550) Aze3 NMeArg5);

wherein Aze represents an L-azetidine carboxylic acid residue, hR represents an L-homoarginine residue and NMeR represents an N-α-methyl arginine residue.

In a further embodiment, the invention provides a non-natural derivative of formula (f) which comprises a peptide having a sequence selected from:

(SEQ ID NO: 56)
-C$_i$-S-F-P-Y-[hR]-C$_{ii}$-V-Y-Y-P-D-I-C$_{iii}$-

((06-550) HArg5);

(SEQ ID NO: 58)
-C$_i$-S-F-[Aze]-Y-[hR]-C$_{ii}$-V-Y-Y-P-D-I-C$_{iii}$-

((06-550) Aze3 HArg5);

(SEQ ID NO: 59)
-C$_i$-S-F-P-Y-[NMeR]-C$_{ii}$-V-Y-Y-P-D-I-C$_{iii}$-

((06-550) NMeArg5);
and (SEQ ID NO: 60)
-C$_i$-S-F-[Aze]-Y-[NMeR]-C$_{ii}$-V-Y-Y-P-D-I-C$_{iii}$-

((06-550) Aze3 NMeArg5);

wherein Aze represents an L-azetidine carboxylic acid residue, hR represents an L-homoarginine residue and NMeR represents an N-α-methyl arginine residue.

Cross-reactivity of these modified peptides between human, rat and rabbit kallikrein may be seen in Table 7.

In a yet further embodiment, the invention provides a modified derivative of formula (f) which comprises a peptide having a sequence selected from:

(SEQ ID NO: 56)
-C$_i$-S-F-P-Y-[hR]-C$_{ii}$-V-Y-Y-P-D-I-C$_{iii}$- ((06-550)

HArg5);
and (SEQ ID NO: 58)
-C$_i$-S-F-[Aze]-Y-[hR]-C$_{ii}$-V-Y-Y-P-D-I-C$_{iii}$-

((06-550) Aze3 HArg5);

wherein Aze represents an L-azetidine carboxylic acid residue and hR represents an L-homoarginine residue.

The peptides of this embodiment are demonstrated to be more suitable than the corresponding N-methyl modified derivatives (see Example 3).

In a still yet further embodiment, the invention provides a non-natural derivative of formula (f) which comprises a peptide having a sequence selected from -C$_i$-S-F-[Aze]-Y-[hR]-C-V-Y-Y-P-D-I-C$_{iii}$- ((06-550) Aze3 HArg5) (SEQ ID NO: 58) wherein Aze represents an L-azetidine carboxylic acid residue and hR represents an L-homoarginine residue.

The peptide of this embodiment is demonstrated to be well tolerated because both the human and rat affinities are high (see Example 3 and Table 7).

In one embodiment, the modified derivative comprises the addition of a spacer group. In a further embodiment, the modified derivative comprises the addition of a spacer group to the N-terminal cysteine (C$_i$) and/or the C-terminal cysteine (C$_{iii}$). In a yet further embodiment, the modified derivative comprises the addition of a spacer group to the C-terminal cysteine (C$_{iii}$). In a still yet further embodiment the spacer group comprises one or more sarcosine groups (suitably 3 sarcosine groups) linked to two or more D-arginine residues (suitably 2 D-arginine residues). Data is presented herein which demonstrates that the presence of such a spacer enhances aqueous solubility of the bicyclic peptide ligands.

In one embodiment, the invention provides a modified derivative of formula (a) which comprises a peptide having a sequence selected from -C$_i$-N-T-W-N-P-W-C-P-W-D-A-P-L-C$_{iii}$-A-Sar$_3$-(D-Arg)$_2$ ((06-259-02 (Sar$_3$-(D-Arg)$_2$) (SEQ ID NO: 61); wherein Sar$_3$ represents 3 sarcosine spacers and (D-Arg)$_2$ represents 2 D-arginine residues.

The peptide of this embodiment demonstrated a favourable in vivo pharmacokinetic profile as described in Example 4. In particular, the peptide demonstrated a marked stability in the rat circulation, as its clearance is mostly driven by renal filtration. Furthermore, the peptide of this embodiment also demonstrated highly significant inhibition of carrageenan-induced paw swelling as described in Example 6 which was comparable to the gold standard (indomethacin) for such a model.

In one embodiment, the invention provides a modified derivative of formula (f) which comprises a peptide having a sequence selected from:

(SEQ ID NO: 62)
-C$_i$-S-F-P-Y-R-C$_{ii}$-V-Y-Y-P-D-I-C$_{iii}$-A-Sar$_3$-(D-Arg)$_2$ ((06-550)-Sar$_3$-(DArg$_2$));
and (SEQ ID NO: 63)
-C$_i$-S-F-[Aze]-Y-[hR]-C$_{ii}$-V-Y-Y-P-D-I-C$_{iii}$-A-Sar$_3$-

(D-Arg)$_2$ ((06-550)-Sar$_3$-(DArg$_2$) Aze3 HArg5);

wherein Sar$_3$ represents 3 sarcosine spacers, (D-Arg)$_2$ represents 2 D-arginine residues, Aze represents an L-azetidine carboxylic acid residue and hR represents an L-homoarginine residue.

The peptides of this embodiment are demonstrated to have more favourable aqueous solubility (see Example 3). More importantly, the addition of the Sar$_3$-(D-Arg)$_2$ (SEQ ID NO: 98) group is well tolerated because potencies remain unchanged compared to the peptides lacking this modification (see Example 3 and Table 7).

In a further embodiment, the invention provides a modified derivative of formula (f) which comprises a peptide having a sequence selected from -C$_i$-S-F-[Aze]-Y-[hR]-C$_{ii}$-V-Y-Y-P-D-I-C$_{iii}$-A-Sar$_3$-(D-Arg)$_2$ ((06-550)-Sar$_3$-(DArg$_2$) Aze3 HArg5) (SEQ ID NO: 63); wherein Sar$_3$ represents 3 sarcosine spacers, (D-Arg)$_2$ represents 2 D-arginine residues, Aze represents an L-azetidine carboxylic acid residue and hR represents an L-homoarginine residue. The peptide of this embodiment is demonstrated in Example 3 to have high stability because few degradation products were observed. Furthermore, the peptide of this embodiment also demonstrated a favourable in vivo pharmacokinetic profile as described in Example 4. Furthermore, the peptide of this embodiment demonstrated slow clearance from the vitreous humour following intravitreal injection into a rabbit eye as described in Example 5. Being in itself already advantageous, this property additionally provides the advantage of being ideally suited for a slow-release formulation for administration to the eye.

In one embodiment, the modified derivative comprises replacement of one or more oxidation sensitive amino acid residues with one or more oxidation resistant amino acid residues. In a further embodiment, the modified derivative comprises replacement of a tryptophan residue with a phenylalanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (were the peptide drug administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises an N-alkylated derivative of one or more amide bonds within the bicyclic peptide ligand. This embodiment is believed to impart proteolytic protection by direct modification of the scissile amide bond (Fiacco et al, Chembiochem. (2008), 9(14), 2200-3). N-methylation is also believed to have a strong effect on the torsional angles of the peptide bond, and is believed to aid in cell penetration & oral availability (Biron et al (2008), Angew. Chem. Int. Ed., 47, 2595-99)

In one embodiment, the modified derivative comprises replacement of one or more peptide bonds with a surrogate bond selected from one or more of an N-alkylated derivative (e.g. —CO—NR), a reduced peptide bond (e.g. —CH$_2$—NH—), a peptoid bond (e.g. —NR—CH$_2$—CO—), a thio amide bond (e.g. —CS—NH—), an azapeptide bond (e.g. —CO—NH—NR—), a trans-alkene bond (e.g. —RHC=C—), a retro-inverso bond (e.g. —NH—CO—) and a urea surrogate bond (e.g. —NH—CO—NHR—).

In one embodiment, the modified derivative comprises removal of any alanine amino acid residues. This embodiment provides the advantage of removing potential proteolytic attack site(s).

In one embodiment, the modified derivative comprises peptide backbone length modification. In a further embodiment, the peptide backbone length modification comprises the use of one or more β$^{2/3}$-amino acid residues (such as —NH—CR—CH$_2$—CO or —NH—CH$_2$—CHR—CO—).

In one embodiment, the modified derivative comprises substitution on the α-carbon of one or more amino acid residues. This embodiment provides the advantage of constraining backbone conformations. In a further embodiment, the modified derivative comprises replacement of one or more amino acid residues with 2-aminoisobutyric acid (also known as α-aminoisobutyric acid (AIB), α-methylalanine or 2-methylalanine).

It should be noted that each of the above mentioned modifications serve to deliberately improve the potency of the peptide against the target. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Binding Activity

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues ($C_i$, $C_{ii}$ and $C_{iii}$) on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris(bromomethyl)mesitylene. This molecule is similar to 1,3,5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

Functional groups include drugs, such as cytotoxic agents for cancer therapy. These include: Alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/prodrug therapy, where the peptide ligand replaces antibodies in ADEPT.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard protein chemistry may be used to introduce an activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum, and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

It will be appreciated that when the peptides ligands of the invention are formulated as ophthalmic compositions for the treatment of ophthalmic disorders, the route of administration will typically be directly to the site of the ophthalmic disorder, such as administration by an ocular route, such as topical, subconjunctival, sub-Tenon, intraocular, ocular implants etc. In one embodiment, the route of administration is by intraocular injection. In an alternative embodiment the ophthalmic composition is delivered topically (e.g. extraocular application) or systemically (e.g. oral or other parenteral route such as for example subcutaneous administration) provided that a sufficient amount of the peptide within cells or tissue located in an eye or adjacent an eye achieves contact with the site of the ophthalmic condition. In an alternative embodiment the ophthalmic composition is delivered parenterally. The precise route of administration will be immediately apparent to the skilled person when addressing the ophthalmic disorder to be treated in accordance with common general knowledge and methodology described in WO 2007/104541, the contents of which are herein incorporated by reference.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, N.Y.).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

Thus, according to a further aspect of the invention, there is provided a peptide ligand as defined herein for use in preventing, suppressing or treating inflammatory states, allergic hypersensitivity, cancer, bacterial or viral infection, and autoimmune disorders.

According to a further aspect of the invention, there is provided a method of preventing, suppressing or treating inflammatory states, allergic hypersensitivity, cancer, bacterial or viral infection, ophthalmic disorders and autoimmune disorders which comprises administering to a patient in need thereof a peptide ligand as defined herein.

In one embodiment, the ophthalmic disorders of the invention are disorders related to impaired retinal vessel permeability and/or integrity. In a further embodiment, the ophthalmic disorders of the invention are disorders related to retinal microvessel rupture leading to focal hemorrhages. In a further embodiment, the ophthalmic disorders of the present invention are back of the eye diseases, in particular retinal diseases. In a further embodiment, the ophthalmic disorders of the invention are front of the eye diseases. In a further embodiment, the ophthalmic disorders of the invention are disorders associated with excessive vascular permeability and/or edema in the eye.

Examples of suitable "ophthalmic disorders" (including exudative and/or inflammatory ophthalmic disorders, disorders related to impaired retinal vessel permeability and/or integrity, disorders related to retinal microvessel rupture leading to focal hemorrhages, back of the eye diseases, retinal diseases and front of the eye diseases) include but are not limited to: age related macular degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, acute macular neuroretinopathy, central serous chorioretinopathy, chorioretinopathy, choroidal neovascularization, neovascular maculopathy, neovascular glaucoma, obstructive arterial and venous retinopathies (e.g. retinal venous occlusion or retinal arterial occlusion), central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, macular oedema occuring as a result of aetiologies such as disease (e.g. diabetic macular oedema), eye injury or eye surgery; retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, thygeson keratitis, progressive mooren's ulcer, an ocular inflammatory disease caused by bacterial or viral infection, and by an ophthalmic operation, an ocular inflammatory disease caused by a physical injury to the eye, a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

References herein to "back-of-eye diseases" include diseases affecting among other the retina, macular, fovea in the posterior region of the eye. Examples of suitable "back-of-eye diseases" include but are not limited to: macular oedema such as clinical macular oedema or angiographic cystoid macular oedema arising from various aetiologies such as diabetes, exudative macular degeneration and macular oedema arising from laser treatment of the retina, age-related macular degeneration, retinopathy of prematurity (also known as retrolental fibroplasia), retinal ischemia and choroidal neovascularization, retinal diseases (diabetic retinopathy, diabetic retinal oedema, retinal detachment, senile macular degeneration due to sub-retinal neovascularization, myopic retinopathy); inflammatory diseases; uveitis associated with neoplasms such as retinoblastoma or pseudoglioma; neovascularization following vitrectomy; vascular diseases (retinal ischemia, choroidal vascular insufficiency, choroidal thrombosis, retinopathies resulting from carotid artery ischemia); and neovascularization of the optic nerve.

References herein to "front-of-eye diseases" refers to diseases affecting predominantly the tissues at the front-of-eye, such as the cornea, iris, ciliary body, conjunctiva etc. Examples of suitable "front-of-eye diseases" include but are not limited to: corneal neovascularization (due to inflammation, transplantation, developmental hypoplasia of the iris, corneal diseases or opacifications with an exudative or inflammatory component, neovascularization due to penetration of the eye or contusive ocular injury; chronic uveitis; anterior uveitis; inflammatory conditions resulting from surgeries such as LASIK, LASEK, refractive surgery, IOL implantation; irreversible corneal oedema as a complication of cataract surgery; oedema as a result of insult or trauma (physical, chemical, pharmacological, etc); inflammation; conjunctivitis (e.g. persistent allergic, giant papillary, seasonal intermittent allergic, perennial allergic, toxic, conjunctivitis caused by infection by bacteria, viruses or Chlamydia); keratoconjunctivitis (vernal, atopic, sicca); iridocyclitis; iritis; scleritis; episcleritis; infectious keratitis; superficial punctuate keratitis; keratoconus; posterior polymorphous dystrophy; Fuch's dystrophies (corneal and endothelial); aphakic and pseudophakic bullous keratopathy; corneal oedema; scleral disease; ocular cicatrcial pemphigoid; pars planitis; Posner Schlossman syndrome; Behcet's disease; Vogt-Koyanagi-Harada syndrome; hypersensitivity reactions; ocular surface disorders; conjunctival oedema; toxoplasmosis chorioretinitis; inflammatory pseudotumor of the orbit; chemosis; conjunctival venous congestion; periorbital cellulitis; acute dacryocystitis; non-specific vasculitis; sarcoidosis; and cytomegalovirus infection.

Examples of suitable "disorders associated with excessive vascular permeability and/or edema in the eye", e.g. in the retina or vitreous, include, but are not limited to, age-related macular degeneration (AMD), retinal edema, retinal hemorrhage, vitreous hemorrhage, macular edema (ME), diabetic macular edema (DME), proliferative diabetic retinopathy (PDR) and non-proliferative diabetic retinopathy (DR), radiation retinopathy, telangiectasis, central serous retinopathy, and retinal vein occlusions. Retinal edema is the accumulation of fluid in the intraretinal space. DME is the result of retinal microvascular changes that occur in patients with diabetes. This compromise of the blood-retinal barrier leads to the leakage of plasma constituents into the surrounding retina, resulting in retinal edema. Other disorders of the retina include retinal vein occlusions (e.g. branch or central vein occlusions), radiation retinopathy, sickle cell retinopathy, retinopathy of prematurity, Von Hippie Lindau disease, posterior uveitis, chronic retinal detachment, Irvine Gass Syndrome, Eals disease, retinitis, and/or choroiditis.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Methods for the testing of systemic lupus erythematosus (SLE) in susceptible mice are known in the art (Knight et al. (1978) J Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J; Immunol., 138: 179).

The invention is further described below with reference to the following examples.

EXAMPLES

Materials and Methods

Cloning of Phaqe Libraries

Phage libraries were generated according to Heinis et al., *Nat Chem Bio* 2009, 5 (7), 502-7.

Phage Selections

Glycerol stocks of phage libraries were diluted to $OD_{600}=0.1$ in 500 ml 2YT/chloramphenicol (30 mg/ml) cultures and phage were produced at 30° C. overnight (15-16 hrs). Phage were purified and chemically modified as described in Heinis, et al., *Nat Chem Biol* 2009, 5 (7), 502-7 Biotinylated hPK (3 mg) (IHPKA, from human plasma, Innovative Research, Novi, Mich., USA) was incubated with 50 ml pre-washed magnetic streptavidin beads (Dynal, M-280 from Invitrogen, Paisley, UK) for 10 minutes at RT. Beads were washed 3 times prior to blocking with 0.5 ml washing buffer (10 mM Tris-Cl, pH 7.4, 150 mM NaCl, 10 mM $MgCl_2$, 1 mM $CaCl_2$) containing 1% BSA and 0.1% Tween 20 for 30 minutes at RT with rotation. Chemically modified phage (typically $10^{10}$-$10^{11}$ t.u. dissolved in 2 ml washing buffer) were concomitantly blocked by addition of 1 ml washing buffer containing 3% BSA and 0.3% Tween 20. Blocked beads were then mixed with the blocked chemically modified phage and incubated for 30 minutes on a rotating wheel at RT. Beads were washed 8 times with washing buffer containing 0.1% Tween 20 and twice with washing buffer before incubation with 100 ml of 50 mM glycine, pH 2.2 for 5 minutes. Eluted phage were transferred to 50 ml of 1 M Tris-Cl, pH 8 for neutralization, incubated with 30 ml TG1 cells at $OD_{600}=0.4$ for 90 minutes at 37° C. and the cells were plated on large 2YT/chloramphenicol plates. One or two additional rounds of panning were performed using the same procedures. In the second round of selection, neutravidin-coated magnetic beads were used to prevent the enrichment of streptavidin-specific peptides. The neutravidin beads were prepared by reacting 0.8 mg neutravidin (Pierce, Rockford, Ill., USA) with 0.5 ml tosyl-activated magnetic beads (Dynal, M-280 from Invitrogen, Paisley, UK) according to the supplier's instructions.

The standard selection process was used with the 5×5 and 6×6 libraries using decreasing concentrations of biotinylated human kallikrein for rounds one and two and then either human or rat biotinylated kallikrein at rounds three and four. The human kallikrein is non-recombinant and therefore the heavy chain is present, the rat kallikrein is recombinant, lacks the heavy chain and possibly has lower activity than expected (based on the activity of the human protein). As there is possibly less activity, the concentration of the rat target was not decreased as far as for the human protein.

Cloning and Expression of Human, Monkey and Rat PK

The catalytic domain of human, monkey and rat PK was expressed in mammalian cells as an inactive precursor having a pro-peptide connected N-terminally via a proTEV cleavage site to the catalytic domain. The expression vector was cloned and the protein expressed, activated and purified as described as follows. Synthetic genes coding for a PK signal sequence, a polyhistidine tag, a proTEV cleavage site, mature catalytic domain of PK and a stop codon were purchased from Geneart (Regensburg, Germany) (Supplementary materials). Plasmid DNA containing the synthetic genes for human, monkey (Macaca mulatta) and rat PK was prepared and the gene transferred into the pEXPR-IBA42 mammalian expression vector (IBA Biotechnology, Göttingen, Germany) using the restriction enzyme pair Xhol and HindIII (Fermentas, Vilnius, Latvia) and T4 DNA ligase (Fermentas). The ligated plasmids were transformed into XL-1 blue electrocompetent cells (Stratagene, Santa Clara, USA) and plated onto 2YT agar plates containing ampicillin (10 µg/ml). DNA from the three expression vectors (termed mPK, rPK and hPK) was produced and the correct sequences confirmed by DNA sequencing (Macrogen, Seoul, South Korea).

The three orthologous plasma kallikreins were expressed in mammalian cells as follows. 50 ml of suspension-adapted HEK-293 cells were grown in serum-free ExCell 293 medium (SAFC Biosciences, St. Louis, Mo.) in the presence of 4 mM glutamine and the histone deacetylase inhibitor valproic acid (3.75 mM) in an orbitally shaken 100 ml flask at 180 rpm in an ISF-4-W incubator (Kühner AG, Birsfelden, Switzerland) at 37° C. in the presence of 5% $CO_2$.

The embryonic kidney (HEK-293) cells at high cell density (20×10⁶ cells/ml) (Backliwal, et al. *Biotechnol Bioeng* 2008, 99 (3), 721-7) were transfected with the three plasmids (300 mg/ml) using linear polyethylenimine (PEI, Polysciences, Eppenheim, Germany). At the end of the 7-day production phase, cells were harvested by centrifugation at 2500 rpm for 15 min at 4° C. Any additional cell debris was removed from the medium by filtration through 0.45 µm PES membranes (Filter-top 250 ml low protein binding TPP). The polyhistidine-tagged protein was purified by Ni-affinity chromatography using Ni-NTA resin, washing buffer (500 mM NaCl, 25 mM $Na_2HPO_4$, pH 7.4) and elution buffer (500 mM NaCl, 25 mM $Na_2HPO_4$, pH 7.4, 500 mM imidazole). The protein was partially activated with (50 units) proTEV (Promega, Madison, Wis., USA) and additionally purified by Ni-affinity chromatography and gel filtration (PD10 column, 150 mM NaCl, 0.5 mM EDTA, 50 mM HEPES, pH 7).

Development of Polypeptides with Improved Binding Activity

Randomisation of Individual Positions

Library construction: In order to map the amino-acids in the kallikrein binding bicyclic peptides a set of small libraries was constructed. For a bicycle comprised of 2 loops of 5 residues, 10 separate libraries were generated each with randomisation at a particular codon in the peptide sequence. Oligonucleotides were designed for each library in order to mutate the phage genome DNA by site-directed mutagenesis. The mutagenesis incorporated randomisation of the codon of interest (change to NNS), and removal of a unique ApaL1 restriction site from the template genome sequence. The mutagenesis product was purified using QIAgen QIAquick PCR purification kit with elution into ultrapure water. Each library was used to separately transform TG1 *E coli* by electroporation with a BioRad Micropulser machine (Ec1 program) and 1 mm BioRad cuvette. After 1 hour recovery at 37° C. in 1 ml SOC media, the library transformants were grown overnight in 25 ml 2TY broth containing antibiotic to selectively grow library transformants only. The bacteria were harvested by centrifugation and the library phage DNA was purified from the *E. coli* using a QIAgen Plasmid Plus Midi kit and eluted in distilled water. The purified DNA was digested with ApaL1 for 2 hours in New England Biolabs buffer 4 to remove the parent material. After digestion, the DNA was repurified using QIAgen PCR purification kit (as above) and used to transform TG1 (electroporation; as described above). Following the 1 hour recovery in SOC, transformants were plated on LB-agar plates containing selective antibiotic and colonies allowed to grow overnight at 37 C.

Assay of binding of individual clones: Library transformant colonies were picked at random and grown as individual cultures in 2TY broth containing selective antibiotic. The picked colonies were DNA-sequenced using a QIAgen PyroMark Q96 DNA sequencer to reveal the amino-acid substitution present in each clone. Where isolated, a clone of each unique substitution was assayed for human plasma kallikrein binding as follows. The phage-containing supernatant was harvested from the culture and phage were cyclised with tris bromomethyl benzene (TBMB) based on the methods of Heinis et al (Nature Chemical Biology vol. 5 pp 502-507 (2009)). The purified phage from this process were assayed for binding to biotinylated human plasma kallikrein using a homogeneous plate-based binding assay; assay read-out measured on a BMG Labtech Pherastar FS plate reader. The quantitative binding data from triplicate assay samples was averaged (mean) and expressed as signal: background (where background was a sample assayed with no target material). The signal:background was expressed as a % of the parallel parent sample. Error bars denote standard deviation of the mean. Assays shown are representative of at least 2 independent experiments. The assay data was correlated with the peptide sequences. Substitutions marked in grey were not tested (a clone was not isolated from the random library sampling). A sample of a non-binding (arbitrary) bicycle was assayed in parallel to illustrate the assay baseline.

Randomisation of Peptide Domains

Library construction: Small phage libraries were generated according to the methods of Heinis et al as described in 'Cloning of phage libraries' above. The sficx3ba primer was modified such that the bicycle-encoding portion was based on a parent 5×5 or 6×6 bicycle (5×5: two 5-residue loops, 6×6: two 6-residue loops) DNA sequence with only 4-6 codons randomized to NNS. The randomized codons were those encoding the peptide domain/motif of interest.

Assay of binding of individual clones: Library transformant colonies, or selection output colonies, were picked and grown as individual cultures in 2TY broth containing selective antibiotic. The picked colonies were DNA-sequenced using a QIAgen PyroMark Q96 DNA sequencer to reveal the amino-acid substitution present in each clone, and were assayed for human plasma kallikrein binding as follows. The phage-containing supernatant was harvested from the culture and phage were cyclised with tris-bromomethylbenzene (TBMB) based on the methods of Heinis et al (Nature Chemical Biology vol. 5 pp 502-507 (2009)). The purified phage from this process were assayed for binding to biotinylated human plasma kallikrein using a homogeneous plate-based binding assay; assay read-out measured on a BMG Labtech Pherastar FS plate reader. The quantitative binding data from duplicate assay samples was averaged (mean) and expressed as signal:background. Assay data shown is representative of at least 2 independent experiments. The assay data was correlated with the peptide sequences.

Peptide Synthesis

Peptide synthesis was based on Fmoc chemistry, using a Symphony peptide synthesiser manufactured by Peptide Instruments. Standard Fmoc-amino acids were employed (Sigma, Merck), with the following side chain protecting groups: Arg(Pbf); Asn(Trt); Asp(OtBu); Cys(Trt); Glu (OtBu); Gln(Trt); His(Trt); Lys(Boc); Ser(tBu); Thr(tBu); Trp(Boc), Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed at 100 µmole scale using 0.37 mmol/gr Fmoc-Rink amide AM resin (AGTC), Fmoc-amino acids were utilised at a four-fold excess, and base was at a four-fold excess with respect to the amino acids. Amino acids were dissolved at 0.2M in DMF, HCTU at 0.4M in DMF, and DIPEA at 1.6M in N-methylpyrrolidone (Alfa Aesar). Coupling times were generally 30 minutes, and deprotection times 2×2.5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H$_2$O/iPr$_3$SiH/dithiothreitrol for 3 hours. Following cleavage, the spent resin was removed by filtration, and the filtrate was added to 35 mL of diethylether that had been cooled at −80° C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in H$_2$O, supplemented with 0.5 mL of 1 M dithiothreitrol, and loaded onto a C8 Luna preparative HPLC column (Phenomenex). Solvents (H$_2$O, acetonitrile) were acidified with 0.1% heptafluorobutyric acid. The gradient ranged from 30-70% acetonitrile in 15 minutes, at a flowrate of 15/20 mL/min, using a Gilson preparative HPLC system. Fractions containing pure linear peptide material (as identified by MALDI) were combined, and modified with trisbromomethylbenzene (TBMB, Sigma). For this, linear peptide was diluted with H$_2$O up to ~35 mL, ~500 µL of 100 mM TBMB in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

All amino acids, unless noted otherwise, were used in the L-configurations.

Bicyclic peptides directly identified from the phage selections usually contained two invariant alanines on the N/C termini. For peptides pursued in plasma stability and pharmacokinetic studies, peptides were resynthesised as indicated, lacking the terminal alanines, and N-terminally acetylated as indicated.

Peptides used for the pharmacokinetic studies in Example 4 were lyophilised from 10 mM HCl in water 3 times to afford the hydrochloride salts of the compounds. Solutions were dosed by intravenous bolus at 1 mg/mL in 50 mM Hepes pH 7.0, 5% glycerol, 1.9% DMSO for two compounds (Ac-(06-550) Aze3 HArg5 Sar$_3$-(D-Arg2)) and (06-259-02)-Sar$_3$-(D-Arg2)) at 5 mg/kg in Spraguely Dawely rats. Serial blood samples (~0.2 mL) were taken into EDTA tubes at the indicated time points, and plasma was separated by centrifugation, and frozen at −20 C for analysis. Employing standard bioanalytical techniques, plasma samples were then analysed and quantified for parent remaining compound using a Waters, Xevo TQS LC-MS. PK parameters were determined using the software package PK Solutions 2.0 from Summit Research Services.

Peptides used for the studies in Example 5 and 6 were obtained from pure (>95%) fractions collected from reverse phase purifications run in the presence of 0.5% acetic acid, which, after lyophilization, afforded the acetate salts of the peptides.

Enzyme Assays

Functional enzyme assays were conducted in 10 mM Tris HCl, 150 mM NaCl, 10 mM MgCl$_2$, 1 mM CaCl$_2$ and 1 mg/mL BSA (all Sigma UK) pH 7.4 at 25° C. in solid black 96 or 384 well plates. Briefly 26.5 pM human plasma kallikrein (purchased from Stratech, UK) or 13.25 pM rat plasma kallikrein (expressed and purified in house) were incubated in the absence or presence of increasing concentrations of test peptide for 15 minutes before addition of the fluorogenic substrate Z-PheArg-AMC (Enzo Lifesciences UK) to a final assay concentration of 100 µM in 4% DMSO. Release of AMC was measured using a Pherastar FS (BMG Labtech), excitation 360 nm, emission 460 nm. The rate of the linear phase of the reaction, typically 5 to 45 minutes, was calculated in MARS data analysis software (BMG labtech). The rate was then used to calculate the IC$_{50}$ and K$_i$ in Prism (GraphPad). A four parameter inhibition non-linear regression equation was used to calculate the IC$_{50}$. The One site-fit K$_i$ equation used to calculate the K$_i$, constraining the K$_i$ to the K$_m$ for the substrate which is 150 µM for the human enzyme, and 200 µM for the rat orthologue. All K$_i$/IC$_{50}$ values are the mean of at least two independent experiments, and at least three for peptides with K$_i$ values lower than 1 nM. For rabbit kallikrein, between 7 to 14 pM enzyme was employed, with 33 µM substrate with a K$_m$ of 50 µM.

Peptides were dissolved as the TFA-salts in their powder form, and stock solutions were usually prepared in water. All solutions were centrifuged and filtered (20 µm syringe filters) prior to absorption measurement at 280 nm. Extinction coefficients were calculated based on the Trp/Tyr content of the peptide, and that of TMB (the TMB core, when contained in a peptide, has an extinction coefficient of ~300 M$^{-1}$ cm$^{-1}$).

Plasma Stability Profiling

Method #1:

A rapid plasma stability profiling assay was developed that employed mass spectrometric detection (MALDI-TOF, Voyager DE, Applied Biosystems) of the parent mass, until the time when the parent peptide mass was no longer observable. Specifically, 200 µM of peptide was incubated in the presence of 35% rat or human plasma (Sera labs, using citrate as anticoagulant) at 37° C., which was supplemented with 1×PBS (derived from a 10×PBS Stock, Sigma). At various time points (i.e. t=0, 3, 24 hrs, henceafter daily up to 10 days), 2 µL of sample was added to 18 µL of 30 mM ammonium bicarbonate in a 1:1 mixture of acetonitrile:H$_2$O. Samples were frozen at −80° C. until the time of analysis. For mass spectrometric analysis that determines the approximate detection window of the peptide, the acetonitrile:H$_2$O-diluted sample of a given time point was spotted directly (0.7 µL) onto the MALDI plate. Matrix (alpha-cyanocinnamic acid, Sigma, prepared as a saturated solution in 1:1 acetonitrile:water containing 0.1% trifluoroacetic acid) was layered over the sample (1 µL). At a similar laser intensity setting on the MALDI TOF, the time could then be determined until parent peptide was no longer detectable. It should be noted that this is a qualitative assay serves to detect relative changes in plasma stability.

Method #2

To obtain stability data more rapidly, peptides were also assessed in 95% plasma. Here, PBS was omitted, and a 1-5 mM peptide stock (in DMSO) was directly diluted into plasma (i.e. 2.5 µL stock into 47.5 µL plasma), giving a final concentration of 50 µM. 5 µL samples were taken at appropriate time points and frozen at −80° C. For analysis, the samples were defrosted, mixed with 25 µL of 3:3:1 acetonitrile:methanol:water, and centrifuged at 13 k for 5 min. 5 µL of the peptide-containing supernatant was aspirated and mixed with 30 mM ammonium bicarbonate in a 1:1 mixture of acetonitrile:H$_2$O. 1 µL of this was then spotted on the MALDI plate and analysed as described above. As above, it should be noted that this is a qualitative assay serves to detect relative changes in plasma stability.

Method #3

To obtain plasma stability quantitatively, peptide stock solutions (1 mM in DMSO) were shipped to Biofocus, UK, who performed the analysis. Peptides were diluted to 100 µM with water, and diluted 1:20 in plasma (5 µM final concentration, with the plasma at 95%), sampled as appropriate, precipitated as above, and quantified by LC-MS using a Waters Xevo TQ-MS.

Example 1: Identification of Kallikrein-Binding Bicyclic Peptides with Favourable Homologue Selectivity and Species Cross-Reactivity (a) Identification of Novel, Potent, Human and Rat Cross-Reactive Lead Sequences For any given therapeutic bicyclic peptide, its pharmacodynamic and pharmacokinetic properties need to be evaluated in preclinical animal species. Common preclinical species include rat, mouse, rabbit, dog, minipig and cynomolgus.

Due to the generally high selectivity of bicyclic peptides, which in part is facilitated by their large contact area to the target protein, high affinity bicyclic peptides to a human target protein may not cross-react with the same target protein derived from a given preclinical species, making preclinical evaluation of such a lead difficult. An example includes PK15 (as disclosed in WO 2009/098450), which is a potent bicyclic peptide (6×6 loop size) with a $K_i$ of ~1.2 nM to human kallikrein. Potency to rat kallikrein is markedly decreased, at a $K_i$ of ~500 nM, making this lead not suitable for preclinical evaluation.

In order to identify 5×5 and 6×6 lead bicyclic peptides with high potency to human kallikrein, whilst retaining appreciable potency to rat kallikrein, phage selections were performed where both the rat and human kallikreins were alternated as baits during each selection round. By adjusting the concentrations of bait during the selection rounds, different cross-reactive lead sequences could be identified. A sample of each selection output was screened for binding to human kallikrein, and subsequently sequenced.

Specifically, the first two selection rounds were performed with human kallikrein, at target concentrations ranging between 3 to 100 nM, followed by two selection rounds using rat kallikrein, at target concentrations of 30 nM.

Screening of individual phage clones for kallikrein binding in the homogeneous screening assay revealed a number of unique sequences with up to 50-fold increase in signal over background. These were prepared as synthetic peptides and assessed for inhibiting the human, rat and rabbit kallikreins (Table 1).

TABLE 1

Summary of novel, cross-reactive bicycle leads

| Bicyclic Peptide Name | SEQ ID No | Human ($K_i$, nM) | Rat ($K_i$, nM) | Rabbit ($K_i$, nM) | Sequence | Format |
|---|---|---|---|---|---|---|
| 06-254 | 68 | 5.3 | 42.5 | 280 | AC<u>KNYWNPCDL</u>VTISCA | 6 × 6 |
| 06-255 | 69 | 3.4 | 18.9 | 342 | AC<u>RNYWNPCTL</u>INITCA | 6 × 6 |
| 06-256 | 70 | 6.6 | 2781.4 | 1457 | AC<u>QKFESR</u>CRVDTRYCA | 6 × 6 |
| 06-257 | 71 | 36.1 | 159.1 | nd | ACPLSDTLCYRRMPPCA | 6 × 6 |
| 06-258 | 72 | 4.3 | 5.2 | 331.3 | AC<u>PYPFRCLHEN</u>LCA | 5 × 5 |
| 06-259 | 73 | 20.1 | 6.2 | nd | AC<u>NTWNPWCGWV</u>GGFCA | 6 × 6 |
| 06-261 | 74 | 0.4 | 4.0 | 1037 | AC<u>NNFPFRC</u>VYYPDICA | 6 × 6 |

Invariant cysteines are in bold, and conserved residues for each lead are underlined.

Several of the leads display good cross-reactivity between rat and human kallikreins: 06-254, 06-255, 06-258, and 06-261 (Table 1). By assessing sequence outputs for each lead family, semi-conserved residues could be identified and are underlined (Table 1).

06-254 and 06-255 share an almost identical first loop, but their second loops differ. 06-258 is the only cross-reactive lead sequence that was identified containing 5 amino acids both in loop 1 and loop 2 (5×5).

(b) Affinity Maturation of Rat-Human Kallikrein Cross-Reactive Bicyclic Peptide Sequences Select bicyclic peptide candidates (Table 1) were selected for affinity maturation. Consensus residues were extrapolated from the initial selection outputs. For affinity maturations, residues that appeared to be outside the consensus region were randomised, according to the information within Table 2.

TABLE 2

Affinity maturation libraries for each kallikrein-binding bicyclic peptide lead

| 06-254 Purpose | Fix predicted motif (underlined); randomise surrounding sequence ("X") | | | | | | | | | | | |
|---|---|---|---|---|---|---|---|---|---|---|---|---|
| Parent sequence | C | <u>K</u> | <u>N</u> | Y | <u>W</u> | <u>N</u> | <u>P</u> C D | <u>L</u> | V | T | I S | C |
| Library | C | <u>K</u> | <u>N</u> | X | <u>W</u> | <u>N</u> | <u>P</u> C D | <u>L</u> | X | X | X X | C |

| 06-256 Purpose | Fix predicted motif (underlined); randomise surrounding sequence ("X") | | | | | | | | | | |
|---|---|---|---|---|---|---|---|---|---|---|---|
| Parent sequence | C | <u>Q</u> | <u>K</u> | <u>F</u> | <u>E</u> | <u>S</u> | <u>R</u> C | R | V | D T RY | C |
| Library | C | <u>Q</u> | <u>K</u> | <u>F</u> | <u>E</u> | <u>S</u> | <u>R</u> C X | X | X | X X X | C |

TABLE 2-continued

Affinity maturation libraries for each kallikrein-binding bicyclic peptide lead

| 06-258 Purpose | Fix predicted motif (underlined); randomise surrounding sequence ("X") | | | | | | | | | | |
|---|---|---|---|---|---|---|---|---|---|---|---|
| Parent sequence | C | P | Y | P | F | R | C | L | H | E | N | L | C |
| Library | C | P | Y | P | X | R | C | X | X | X | X | X | C |

| 06-259 Purpose | Fix predicted motif (underlined); randomise surrounding sequence ("X") | | | | | | | | | | |
|---|---|---|---|---|---|---|---|---|---|---|---|
| Parent sequence | C | N T | W | N | P | W C G | W | V | G | G F | C |
| Library | C | N X | W | N | P | W C X | X | X | X | X X | C |

| 06-261 Purpose | Randomise predicted motif (underlined, ("X")); fix surrounding sequence | | | | | | | | | | |
|---|---|---|---|---|---|---|---|---|---|---|---|
| Parent sequence | C | N N | F | P | F | R C V | Y | Y | P | D I | C |
| Library | C | N N | X | X | X | X C V | Y | Y | P | D I | C |

Sequence ID Numbers: 06-254 parent (SEQ ID NO: 23), library (SEQ ID NO: 64); 06-256 parent (SEQ ID NO: 49), library (SEQ ID NO: 65); 06-258 parent (SEQ ID NO: 52), library (SEQ ID NO: 66); 06-259 parent (SEQ ID NO: 10), library (SEQ ID NO: 67); 06-261 parent (SEQ ID NO: 54), library (SEQ ID NO: 99).

Residues outside the more conserved binding motif were randomised ("X"). In the case of 06-261, its 06-34-18-like FPFR motif (SEQ ID NO: 100) was randomised, while surrounding residues were fixed.

The sequence output of the affinity matured libraries is shown in two examples, 06-254 and 06-259:

06-254 Sequence Output:

Table 3 shows the most potent 06-254 variants identified by the screening assay.

TABLE 3

Sequence output of the 06-254 affinity-matured library

| | PK15 | SEQ ID No | Control | S:B 14.05 |
|---|---|---|---|---|
| 06-254 Top23 | 06-254 parent | 23 | CKNYWNPCDLVTISC | 23.48 |
| | 06-254-01 | 24 | CKNYWNPCDLIETTC | 61.90 |
| | 06-254-02 | 25 | CKNYWNPCDLIPGPC | 46.65 |
| | 06-254-03 | 26 | CKNYWNPCDLVMDTC | 56.70 |
| | 06-254-F4 | 27 | CKNYWNPCDLIQDAC | 46.42 |
| | 06-254-B3 | 28 | CKNYWNPCDLISIKC | 61.60 |
| | 06-254-G3 | 29 | CKNYWNPCDLIPTGC | 37.55 |
| | 06-254-H4 | 30 | CKNYWNPCDLVQIHC | 38.86 |
| | 06-254-G2 | 31 | CKNYWNPCDLIGITC | 46.33 |
| | 06-254-A4 | 32 | CKNYWNPCDLVDTFC | 32.38 |
| | 06-254-G4 | 33 | CKNYWNPCDLVEAQC | 33.15 |
| | 06-254-D3 | 34 | CKNFWNPCDLIPISC | 20.27 |
| | 06-254-E2 | 35 | CKNYWNPCDLIWTDC | 31.45 |

TABLE 3-continued

Sequence output of the 06-254 affinity-matured library

| | PK15 | SEQ ID No | Control | S:B 14.05 |
|---|---|---|---|---|
| | 06-254-F5 | 36 | CKNYWNPCDLIPDLC | 38.67 |
| | 06-254-E5 | 37 | CKNYWNPCDLLESTC | 29.71 |
| | 06-254-D1 | 38 | CKNYWNPCDLIRPPC | 33.64 |
| | 06-254-B9 | 39 | CKNYWNPCDLLGIAC | 37.98 |
| | 06-254-E3 | 40 | CKNYWNPCDLVHDIC | 30.17 |
| | 06-254-D6 | 41 | CKNYWNPCDLIPDMC | 24.36 |
| | 06-254-H3 | 42 | CKNYWNPCDLIADLC | 25.21 |
| | 06-254-A7 | 43 | CKNYWNPCDLLHVRC | 26.12 |
| | 06-254-C1 | 44 | CKNYWNPCDLIAPYC | 27.41 |
| | 06-254-E6 | 45 | CKNYWNPCGLVYSTC | 23.47 |
| | 06-254-B1 | 46 | CKNYWNPCDLLPDLC | 9.99 |

S:B refers to Signal: Background. Potent binders were identified by the homogeneous screening assay, and compared to its parent sequence (06-254) and the 6 x 6 kallikrein binder PK15 (WO 2009/098450).

The most potent candidates (06-254-01, 06-254-02 and 06-254-03) were selected for peptide synthesis, and assessed for rat and human kallikrein inhibition.

06-259 Sequence Output:

Table 4 shows the most potent 06-259 variants identified by the screening assay.

TABLE 4

Sequence output of the 06-259 affinity-matured library

| | PK-15 | SEQ ID No | Control | S:B 14.05 |
|---|---|---|---|---|
| 06-259 Top10 | 06-259 (parent) | 10 | CNTWNPWCGWVGGFC | 1.17 |
| | 06-259-01 | 11 | CNHWNPWCSVEPPVC | 51.67 |
| | 06-259-02 | 12 | CNTWNPWCPWDAPLC | 43.49 |
| | 06-259-03 | 13 | CNHWNPWCSADPPIC | 49.82 |
| | 06-259-04 | 14 | CNYWNPWCPWDAPLC | — |
| | 06-259-F1 | 15 | CNHWNPWCSADPPRC | 38.05 |
| | 06-259-E2 | 16 | CNHWNPWCPADIPVC | 37.69 |
| | 06-259-H3 | 17 | CNHWNPWCSDDPYIC | 38.73 |
| | 06-259-H4 | 18 | CNHWNPWCSSDPPVC | 33.62 |
| | 06-259-A6 | 19 | CNYWNPWCSDTRIGC | 22.58 |
| | 06-259-F2 | 20 | CNTWNPWCSWPDIDC | 22.71 |

S:B refers to Signal:Background. Potent binders were identified by the homogeneous screening assay, and compared to its parent sequence (06-259) and the 6 x 6 kallikrein binder PK15 (WO 2009/098450).

The most potent candidates (06-259-01, 06-259-02, 06-259-03 and 06-259-04) were selected for peptide synthesis and affinity measurement to rat and human kallikrein.

The in vitro potencies and cross-reactivity of the synthetic peptides are summarised in Table 5.

TABLE 5

Summary of the inhibition constants (KJ) towards human, rat and rabbit kallikrein

| Bicycle Name | SEQ ID No | Human (Ki, nM) | Rat (Ki, nM) | Rabbit (Ki, nM) | Sequence | Format |
|---|---|---|---|---|---|---|
| 06-254 | 68 | 5.3 | 42.5 | 280 | ACKNYWNPCDLVTISCA | 6 x 6 |
| 06-254-01 | 75 | 1.0 | 15.9 | nd | ACKNYWNPCDLIETTCA | 6 x 6 |
| 06-254-02 | 76 | 0.5 | 7.6 | nd | ACKNYWNPCDLIPGPCA | 6 x 6 |
| 06-254-03 | 77 | 1.4 | 10.1 | nd | ACKNYWNPCDLVMDTCA | 6 x 6 |
| 06-255 | 69 | 3.4 | 18.9 | 342 | ACRNYWNPCTLINITCA | 6 x 6 |
| 06-256 | 70 | 6.6 | 2780 | 1457 | ACQKFESRCRVDTRYCA | 6 x 6 |
| 06-257 | 71 | 36.1 | 159.1 | nd | ACPLSDTLCYRRMPPCA | 6 x 6 |
| 06-258 | 72 | 4.3 | 5.2 | 331 | ACPYPFRCLHENLCA | 5 x 5 |
| 06-259 | 73 | 20.1 | 6.2 | nd | ACNTWNPWCGWVGGFCA | 6 x 6 |
| 06-259-01 | 78 | 2.4 | 10.4 | nd | ACNHWNPWCSVEPPVCA | 6 x 6 |
| 06-259-02 | 79 | 2.3 | 0.2 | 1448 | ACNTWNPWCPWDAPLCA | 6 x 6 |
| 06-259-03 | 80 | 1.4 | 8.2 | nd | ACNHWNPWCSADPPICA | 6 x 6 |
| 06-259-04 | 81 | 3.4 | 6.7 | nd | ACNYWNPWCPWDAPLCA | 6 x 6 |
| 06-261 | 74 | 0.4 | 4.0 | 1037 | ACNNFPFRCVYYPDICA | 6 x 6 |

Bicyclic peptide leads with dissociation rates lower than 10/20 nM towards human/rat kallikrein, respectively, are indicated in bold.

Altogether, there are several candidates that display high potencies and good cross-reactivity between rat and human kallikrein, such as 06-254-01, 06-254-02, 06-254-03, 06-255, 06-258, 06-259-01, 06-259-02, 06-259-03, 06-259-04 and 06-261 (in bold, see Table 5).

Example 2: Plasma Stability Screen of Kallikrein-Binding Bicyclic Peptides Reveals Promising Lead Candidates In Example 1, several novel bicyclic lead sequences were identified with high human and rat potencies. The most potent member of each family was selected for comparison of rat and human plasma stabilities. These were 06-254-02, 06-255, 06-259-02 and 06-261. Initial screening using Method #1 indicated 06-255 and 06-259-02 to be more stable than the remaining bicyclic peptides, as judged by a longer window of detection of these two peptides (up to 10 days, figures not shown). The remaining peptides were no more detectable after 2-3 days, displaying a similar low stability as the unmodified sequence of 06-34-18.

06-255 and 06-259-02 both suffered from a poor solubility profile, and were thus resynthesised with a solubilising C-terminal extension (Sar$_3$-(D-Arg)$_2$ (SEQ ID NO: 98)). Sarcosine$_3$ (Sar$_3$) hereby serves as a molecular spacer, while the D-arginines impart higher aqueous solubility to the molecule due to their strongly ionic, water-complexing nature at physiological pH.

The solubilising extension did not significantly impede the enzyme inhibition constants, as indicated in Table 6.

TABLE 6

Summary of the inhibition constants (K$_i$) towards human, rat and rabbit kallikrein with solubilizing extension

| Bicycle Name | SEQ ID No | Human | Rat | Rabbit | Sequence | Molecular Weight |
|---|---|---|---|---|---|---|
| Ac-(06-255) | 82 | 3.7 | 7.7 | 342 | Ac-CRNYWNPCTLINITC | 1969.32 |
| Ac-(06-255)-Sar3-(DArg2) | 83 | 1.2 | 7.4 | 251 | Ac-CRNYWNPCTLINITCA-Sar3-DArg2 | 2566.01 |
| Ac-(06-259-02) | 84 | 5.9 | 3.8 | nd | Ac-CNTWNPWCPWDAPLC | 1961.26 |
| Ac-(06-259-02)-Sar3-(DArg2) | 85 | 0.8 | 2.1 | 1448 | Ac-CNTWNPWCPWDAPLCA-Sar3-DArg2 | 2557.95 |

Figure 2:
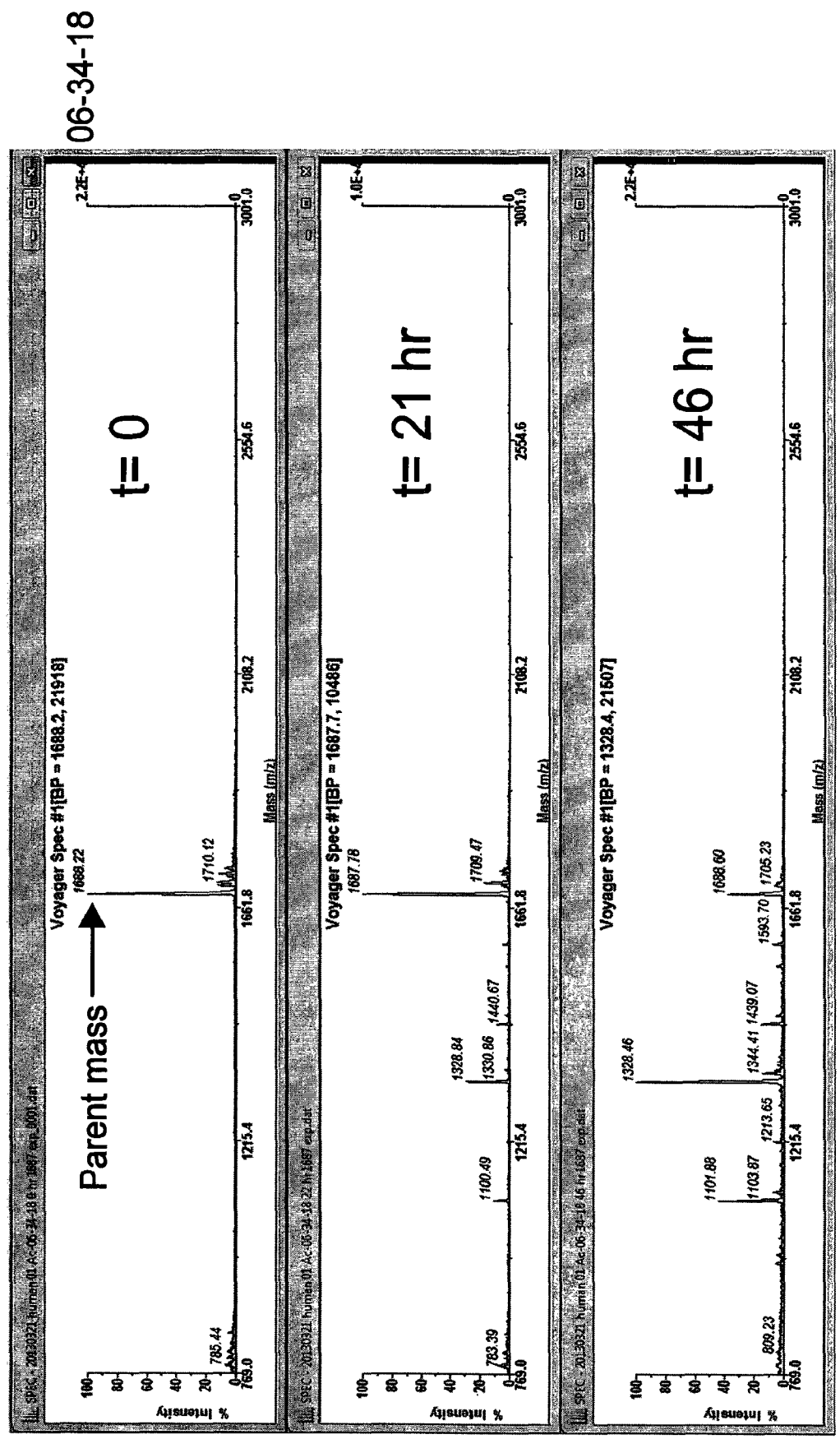
FIG. 2: Comparative human plasma stability of the 06-34-18 control against the cross-reactive novel kallikrein-binding bicycle leads.

Peptides were assayed in human and rat plasma under conditions described in Method #2. Stabilities are assessed comparatively against 06-34-18, which has a quantitative $t_{1/2}$ of 2.3 hrs in rat plasma, and 2 hrs in human plasma (WO 2013/050616). FIGS. 1 and 2 demonstrate that bicyclic peptide lead 06-259-02 has a particularly favourable plasma stability profile, in that it is significantly more stable to both human and rat plasma compared to 06-255 and 06-34-18.

Example 3: Grafting Peptide Loops Between Different Bicyclic Peptide Leads Generates Novel Chimeric Constructs with Favourable Properties The first loop of the previously disclosed 06-34-18 sequence (WO 2013/050616, sequence: ▓SWPAR▓L HQDL▓ (SEQ ID NO: 86)) shares a similar FPFR motif (SEQ ID NO: 100, underlined) with the 06-261 peptide identified herein (sequence: ▓NNFPFR▓VYYPDI▓ (SEQ ID NO: 54)). However, 06-34-18 is described to contain two proteolytic recognition sites that render the peptide labile towards blood plasma proteases and therefore unsuitable as a kallikrein inhibiting therapeutic. These sites comprise residues Arg5 and His7 of 06-34-18 (▓SWPAR▓LHQDL▓ (SEQ ID NO: 86): underlined and bold). In the presently disclosed 06-261 sequence (Example 1), the equivalent histidine proteolytic recognition site in loop 2 is absent.

Due to the lack of His7 in the second loop of 06-261 (sequence: VYYPDI (SEQ ID NO: 87)), the inventors of the present invention replaced the proteolytically labile, histidine-containing second loop of 06-34-18 with the second loop of 06-261 in the hope of yielding a fully potent, chimeric peptide with enhanced proteolytic stability in loop 2. Specifically, this sequence comprises the first loop of 06-34-18 (sequence: SFPYR (SEQ ID NO: 88)) and the second loop of 06-261 (sequence: VYYPDI (SEQ ID NO: 87)), yielding the chimeric full sequence CS FPYRCVYYPDIC (SEQ ID NO: 55) (or the WPAR equivalent, i.e. CSWPARCVYYPDIC (SEQ ID NO: 89)). This chimeric peptide is termed 06-550, and has 5 residues in loop 1, and 6 residues in loop 2.

It had been previously disclosed (WO 2013/050616) that the Arg5-induced proteolytic lability in 06-34-18 can be removed or reduced by replacing Arg5 with N-α-methyl arginine (NMe-Arg) or Homoarginine (HArg). Additionally, a concomitant affinity-enhancing substitution of L-azetidine carboxylic acid (Aze) can be introduced at position 3, replacing the original proline 3.

As the chimeric bicycle peptide 06-550 retains the first loop of 06-34-18, identical modifications on Arg5/Pro3 to HArg5/Aze3 were implemented, and this peptide is termed 06-550 Aze3 HArg5.

Due to the absence of a solubility enhancing Histidine 7 in the sequence, 06-550 (or 06-550 Aze3 HArg5) displayed a significantly reduced aqueous solubility compared to 06-34-18, however. To enhance the aqueous solubility of these molecules, derivatives were synthesised which contained C-terminal extensions comprising sarcosine$_3$-spacers followed by two D-arginines. The inclusion of the D-arginines led to a more favourable aqueous solubility of these peptides.

The kallikrein inhibition constants of these peptides are summarised in Table 7.

TABLE 7

Inhibition constants of 06-550 peptides towards human, rat and rabbit kallikrein

| Bicycle Name | SEQ ID No | Human (Ki, nM) | Rat (Ki, M) | Rabbit (Ki, M) | Sequence | Format |
|---|---|---|---|---|---|---|
| Ac-(06-550) | 90 | 0.9 | 9.3 | 610 | Ac-CSFPYRCVYYPDIC | 5 × 6 |
| Ac-(06-550) HArg5 | 91 | 1.8 | 25 | nd | Ac-CSFPY[HArg]CVYYPDIC | 5 × 6 |
| Ac-(06-550) Aze3 HArg5 | 92 | 0.5 | 5.6 | nd | Ac-CSF[Aze]Y[HArg]CVYYPDIC | 5 × 6 |
| Ac-(06-550) NMe-Arg5 | 93 | 2.66 | nd | nd | Ac-CSFPY[Nme-Arg]CVYYPDIC | 5 × 6 |
| Ac-(06-550) Aze3 NMe-Arg5 | 94 | 53 | nd | nd | Ac-CSF[Aze]Y[NMe-Arg]CVYYPDIC | 5 × 6 |
| Ac-(06-550)-Sar$_3$-(DArg$_2$) | 95 | 2.1 | 24 | 207 | Ac-CSFPYRCVYYPDICA-Sar$_3$-(DArg)$_2$ | 5 × 6 |
| Ac-(06-550)-Sar$_3$-(DArg$_2$) Aze3HArg5 | 96 | 0.4 | 8.2 | 2650 | Ac-CSF[Aze]Y[HArg]CVYYPDICA-Sar$_3$-(DArg)$_2$ | 5 × 6 |

From the data it is clear that the Aze3-HArg5 modification is well tolerated, since both human and rat affinities are high. The N-methyl modification is less suitable. Equally, the Sar$_3$-(D-Arg2) (SEQ ID NO: 98) solubilising extension is well tolerated, as potencies remain unchanged compared to the peptides lacking this extension.

Comparative Plasma Stability Profiling of 06-550 Derivatives

Figure 3:
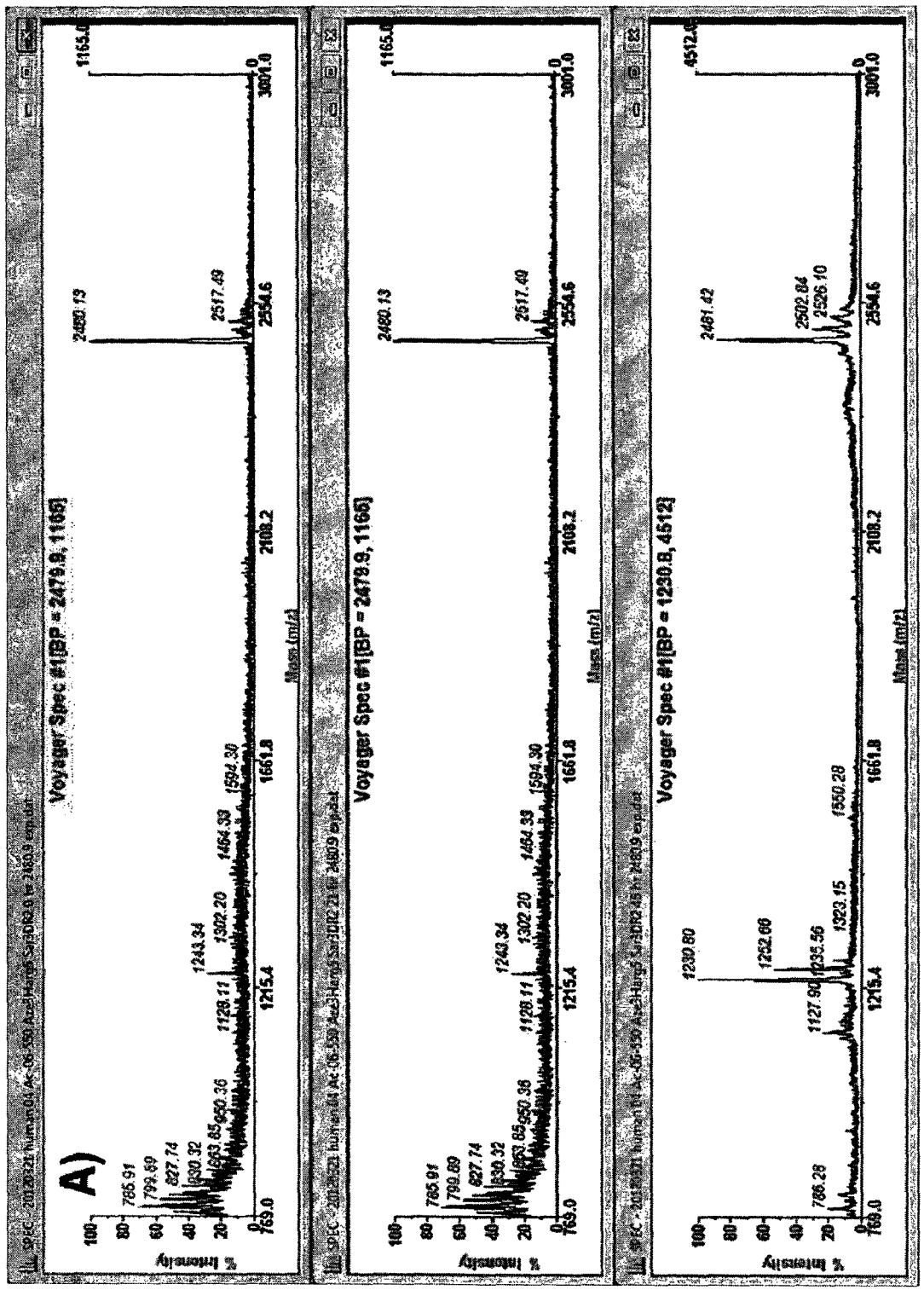
FIG. 3: Comparative stability of a 06-550 derivative in human (A) and rat (B) plasma. The plasma and peptide mixtures were sampled at 0 (top), 21 (middle), and 46 (bottom) hrs. The parent peak of the peptide is at 2481.9 MH$^+$. Little degradation is observed over the time course of 46 hours, as the relative abundance of the parent peak remains high.

The stability of the bicyclic peptide "Ac-(06-550)-Sar$_3$-(DArg2) Aze3 HArg5" (Table 7) was assessed for relative stability in human and rat plasma according to Method #2 (FIG. 3) and compared to the unstable 06-34-18 (FIGS. 1 and 2).

In plasma from both species, the peptide displays high stability, as few degradation products are observed. By comparison, the parent mass of the unstable 06-34-18 has largely disappeared during the same time course (data shown in Example 2). Thus, the concept of combining loops derived from separate parent sequences (06-261 and 06-34-18) has yielded a novel, chimeric, potent and proteolytically stable molecule.

Example 4: In Vivo Pharmacokinetic Behaviour of Select Kallikrein-Inhibiting Bicyclic Peptides Peptides Ac-(06-550)-Sar$_3$-(D-Arg)$_2$Aze3 HArg5 (which contains the stabilising and affinity enhancing modifications Aze3 and HArg5, and a solubilising C-terminal extension Sar$_3$-(D-Arg)$_2$) (SEQ ID NO: 98) and Ac-(06-259-02)-Sar$_3$-(D-Arg)$_2$ were selected for pharmacokinetic assessment in rat. Peptides were injected intravenously in buffered solution at 1 mg/mL at 5 mg/kg Sprague Dawley rats, and blood was sampled and analysed for peptide concentrations at a number of time points post injection.

Example 5: In Vivo Pharmacokinetic Analysis Following Intravitreal Injection of Select Kallikrein-Inhibiting Bicyclic Peptides In this analysis, peptide Ac-(06-550)-Sar$_3$-(D-Arg)$_2$ Aze3 HArg5 (referred to in this study as Bicycle 1 and which contains the stabilising and affinity enhancing modifications Aze3 and HArg5, and a solubilising C-terminal extension Sar$_3$-(D-Arg)$_2$ (SEQ ID NO: 98); see Examples 3 and 4 herein) was assessed comparatively against the peptide Ac-(06-34-18) Phe2 Aze3 Tyr4 HArg5 Ala($\psi$CH$_2$NH)6 (referred to in this study as Bicycle 2 and which is disclosed in Table 26b and FIG. 22 of PCT/EP2014/057440). New Zealand White rabbits (2-3 kg) were anaesthetized and both peptides were administered by intravitreal injection (100 μg/eye) according to the protocol described in Table 9.

TABLE 9

Administration protocol for intravitreal injection

| Group Number | Test Material OS | Test Material OD | Dose Volume (μL/eye) | Concentration/Eye (mg/mL) | Target Termination Time (Post-Dose) | No. of Males |
|---|---|---|---|---|---|---|
| 1 | Vehicle | Vehicle | 50 | 0 | 1 h | 3 |
| 2 | Bicycle 1 | Bicycle 2 | 50 | 2 | 5 min | 3 |
| 3 | Bicycle 1 | Bicycle 2 | 50 | | 15 min | 3 |
| 4 | Bicycle 1 | Bicycle 2 | 50 | | 30 min | 3 |
| 5 | Bicycle 1 | Bicycle 2 | 50 | | 1 h | 3 |
| 6 | Bicycle 1 | Bicycle 2 | 50 | | 4 h | 3 |
| 7 | Bicycle 1 | Bicycle 2 | 50 | | 8 h | 3 |
| 8 | Bicycle 1 | Bicycle 2 | 50 | | 24 h | 3 |
| 9 | Bicycle 1 | Bicycle 2 | 50 | | 48 h | 3 |

Figure 4:
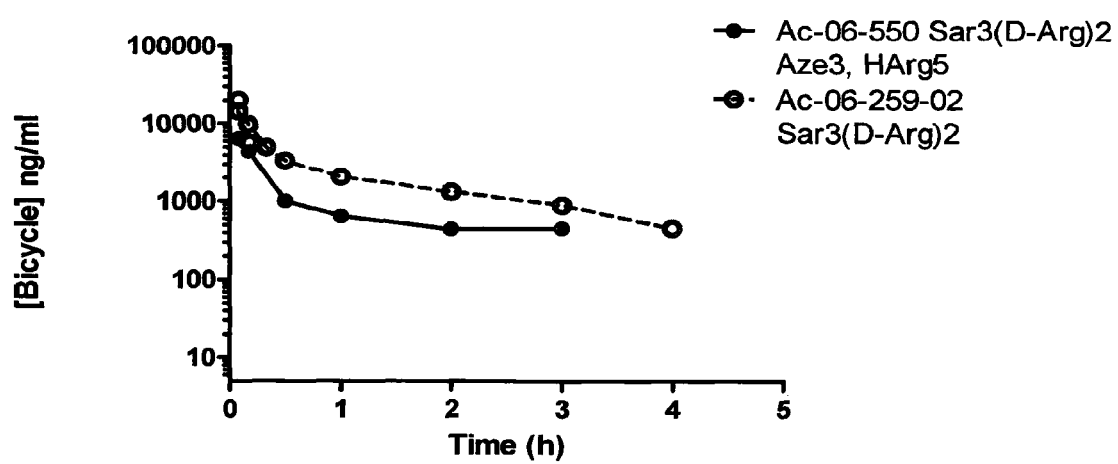
FIG. 4: In vivo pharmacokinetic profile of two selected peptides in rat. The 06-259-02 derivative in particular displays a marked stability in the rat circulation, as its clearance is mostly driven by renal filtration.

OS = left eye;
OD = right eye;
Min = minutes;
h = hours.
Vehicle = 10 mM sodium acetate buffer pH 5.0 in water containing 2.5% glycerol Both peptides displayed a clearance between 17 (06-550) and 7 ml/min/kg (06-259-02) (Table 8, FIG. 4), which is close to the published renal filtration rate in rat (~8-9 mL/min/kg) [Jobin J, Bonjour J P, (1985) Am J Physiol.; 248(5 Pt 2):F734-8].

This underlines the enhanced proteolytic stability of Ac-(06-550)-Sar$_3$-(D-Arg)$_2$ Aze3 HArg5, which contains the two stabilising modifications Aze3 and HArg5 and a sequence in loop two that is inherently proteolytically stable.

In the case of Ac-(06-259-02)-Sar$_3$-(D-Arg)$_2$, the natural sequence is sufficiently proteolytically stable in the rat such that its clearance is mostly driven by renal excretion.

TABLE 8

Pharmacokinetic parameters of Ac-(06-550)-Sar$_3$-(D-Arg)$_2$ Aze3 HArg5 and Ac-(06-259-02)-Sar$_3$-(D-Arg)$_2$ in rat

| Bicyclic Peptide Nomenclature | Clearance (ml/min/kg) | Vss (L/kg) | $t_{1/2\ elimination}$ (min) |
|---|---|---|---|
| Ac-(06-550)-Sar$_3$-(D-Arg)$_2$ Aze3 HArg5 | 17 | 0.4 | 136 |
| Ac-(06-259-02)-Sar$_3$-(D-Arg)$_2$ | 7.2 | 0.8 | 78 |

Figure 5:
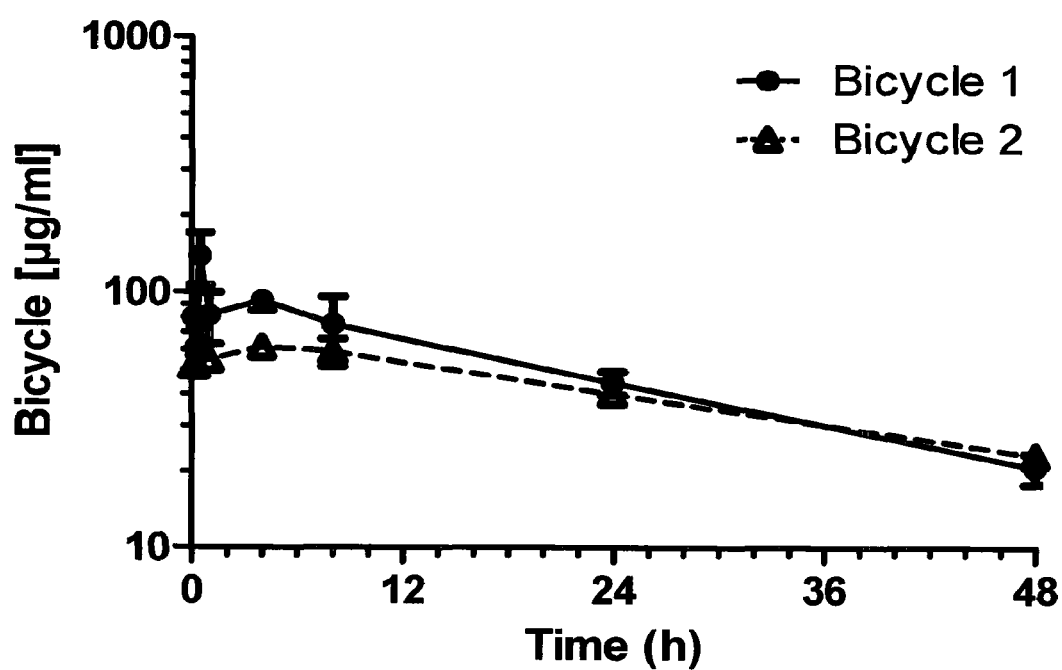
FIG. 5: In vivo pharmacokinetic analysis following intravitreal injection in rabbit of two selected peptides. Both peptides, including the 06-550 derivative, were slowly cleared from the vitreous humour, with an elimination half-life of 20-30 h.

After an appropriate time, rabbits were euthanized and vitreous humour, aqueous humour, retina and plasma samples were taken. Samples were analysed by LC-MS to determine the concentration of the peptide. The results of this study are shown in FIG. 5 where it can be observed that both peptides were slowly cleared from the vitreous humour, with elimination half-lives of 20-30 h. This is significantly slower than the clearance of small molecules such as the antibiotic ciprofloxacin (reported half-life in normal rabbit vitreous 2.2 hrs; Pearson et al. 1993, Retina 13:326-330).

Example 6: Effect of Select Kallikrein-Inhibiting Bicyclic Peptides Upon Carrageenan-Induced Paw Oedema In this analysis, peptide Ac-(06-259-02)-Sar$_3$-(D-Arg)$_2$ (referred to in this study as Bicycle 3; see Example 2 herein) was assessed comparatively against the peptide Ac-(06-34-18) Phe2 Aze3 Tyr4 HArg5 Ala($\psi$CH$_2$NH)6 (referred to in this study as Bicycle 2 and which is disclosed in Table 26b and FIG. 22 of PCT/EP2014/057440). Inflammation was induced in male Sprague-Dawley rats (n=10 per group) by injection of 100 μL of 1% carrageenan solution in the subplantar region of the right hind paw. Animals received treatment with the peptides and indomethacin according to Table 10:

TABLE 10

| Dosage regime for carrageenan-induced analysis | | | | |
|---|---|---|---|---|
| Group | Treatment | Dose (mg/kg) | Dose route | Time* |
| 1 | Vehicle | N/A | ip | −15 min, 2 h 45 min |
| 2 | Indomethacin | 5 | ip | −15 min, |
| 3 | Bicycle 2 | 15 | ip | −15 min, 2 h 45 min |
| 4 | Bicycle 3 | 15 | ip | −15 min, 2 h 45 min |

*dosing times relative to carrageenan administration
ip = intraperitoneal
Vehicle = 50 mM sodium acetate buffer pH 5.0, 20% PEG400 and 10% Kolliphor EL At 1, 2, 4 and 6 hours after carrageenan administration, paw volume was measured by water displacement method. Statistical analysis was conducted using 2-way ANOVA with repeated measures (GraphPad Prism).

Figure 6:
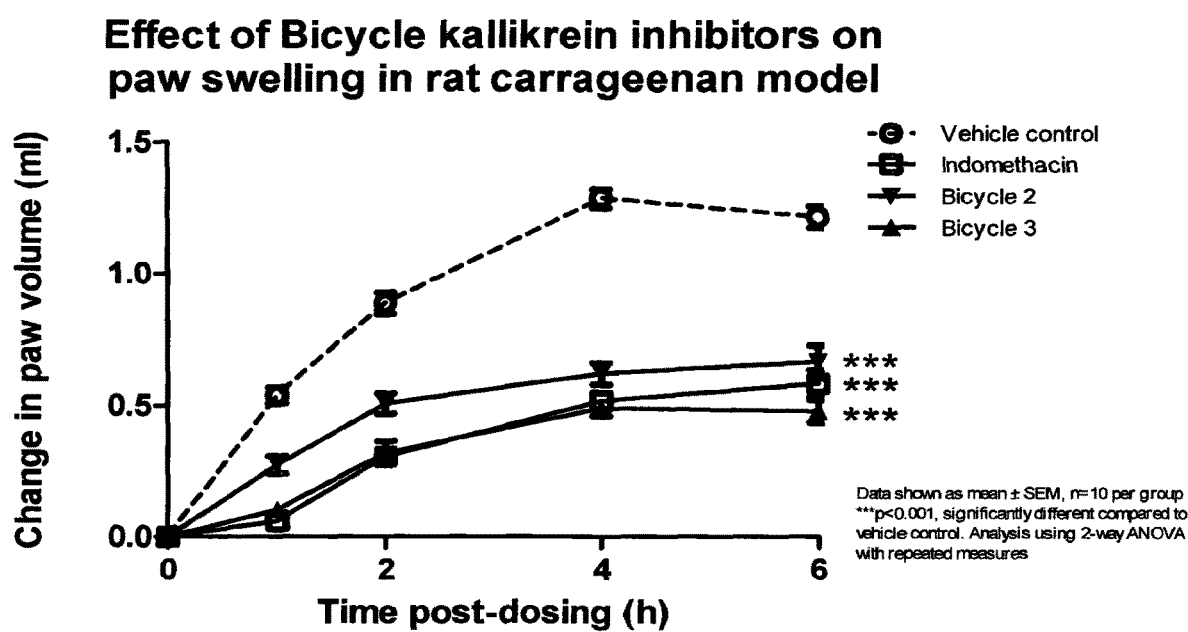
FIG. 6: Effect of two selected peptides upon carrageenan-induced paw oedema. Both peptides, including the 06-259-02 derivative, inhibited the paw swelling induced by carrageenan at all timepoints.

The results of this study are shown in FIG. 6 where it can be observed that both peptides inhibited the paw swelling induced by carrageenan at all timepoints. Treatment with either peptide or the positive control, indomethacin, resulted in a highly significant reduction in paw swelling ($p<0.001$). Importantly, the extent of inhibition was comparable between the two peptides and indomethacin, the latter being considered as the gold standard therapeutic moiety in this model.

The invention claimed is:

1. A peptide ligand specific for plasma kallikrein comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises a peptide sequence of:

$$-C_i-(N)_a-U-J-P-J-R-C_{ii}-V-Y-Y-P-D-I-C_{iii}-, \text{ (SEQ ID NO: 6)}$$

or a modified derivative, or pharmaceutically acceptable salt, thereof;
wherein:
$C_i$, $C_{ii}$ and $C_{iii}$ represent first, second and third cysteine residues, respectively;
subscript "a" represents an integer selected from 0 or 1;
J represents a non-polar aromatic amino acid residue selected from F, W and Y;
U represents a polar, uncharged amino acid residue selected from N, C, Q, M, S and T.

2. The peptide ligand as defined in claim 1, wherein the peptide comprises a sequence of:

$$-C_i-(N)_a-N/S-F-P-F/Y-R-C_{ii}-V-Y-Y-P-D-I-C_{iii}-. \text{ (SEQ ID NO: 53)}$$

3. The peptide ligand as defined in claim 1, wherein the peptide comprises a sequence of:

$$-C_i-N-N-F-P-F-R-C_{ii}-V-Y-Y-P-D-I-C_{iii}- \text{ (06-261); (SEQ ID NO: 54)}$$

or $$-C_i-S-F-P-Y-R-C_{ii}-V-Y-Y-P-D-I-C_{iii}- \text{ (06-550). (SEQ ID NO: 55)}$$

4. The peptide ligand as defined in claim 1, wherein the modified derivative includes one or more modifications selected from: N-terminal and/or C-terminal modifications; replacement of one or more amino acid residues with one or more non-natural amino acid residues; addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the α-carbon of one or more amino acid residues with another chemical group, and post-synthetic bioorthogonal modification of amino acids.

5. The peptide ligand as defined in claim 4, wherein the modified derivative comprises an N-terminal modification.

6. The peptide ligand as defined in claim 5, wherein the N-terminal modification comprises an N-terminal acetyl group.

7. The peptide ligand as defined in claim 5, wherein the N-terminal modification comprises capping an N-terminal cysteine group with acetic anhydride.

8. The peptide ligand as defined in claim 4, wherein the modified derivative comprises a C-terminal modification.

9. The peptide ligand as defined in claim 8, wherein the C-terminal modification comprises a C-terminal amide group.

10. The peptide ligand as defined in claim 8, wherein the C-terminal modification comprises amidation of a C-terminal cysteine group.

11. The peptide ligand as defined in claim 4, wherein the modified derivative comprises replacement of one or more amino acid residues with one or more non-natural amino acid residues.

12. The peptide ligand as defined in claim 11, which is a non-natural derivative comprising a peptide having a sequence selected from:

$$-C_i-S-F-P-Y-[hR]-C_{ii}-V-Y-Y-P-D-I-C_{iii}- \text{ (SEQ ID NO: 56)}$$
((06-550) HArg5);

$$-C_i-S-F-[Aze]-Y-R-C_{ii}-V-Y-Y-P-D-I-C_{iii}-; \text{ (SEQ ID NO: 57)}$$

$$-C_i-S-F-[Aze]-Y-[hR]-C_{ii}-V-Y-Y-P-D-I-C_{iii}- \text{ (SEQ ID NO: 58)}$$
((06-550) Aze3 HArg5);

$$-C_i-S-F-P-Y-[NMeR]-C_{ii}-V-Y-Y-P-D-I-C_{iii}- \text{ (SEQ ID NO: 59)}$$
((06-550) NMeArg5);

$$-C_i-S-F-[Aze]-Y-[NMeR]-C_{ii}-V-Y-Y-P-D-I-C_{iii}- \text{ (SEQ ID NO: 60)}$$
((06-550) Aze3 NMeArg5);

$$-C_i-N-T-W-N-P-W-C_{ii}-P-W-D-A-P-L-C_{iii}-A-Sar_3- \text{ (SEQ ID NO: 61)}$$
(D-Arg)$_2$ ((06-259-02 (Sar$_3$-(D-Arg)$_2$);

-continued (SEQ ID NO: 62)
-C$_i$-S-F-P-Y-R-C$_{ii}$-V-Y-Y-P-D-I-C$_{iii}$-A-Sar$_3$-((D-Arg)$_2$
(06-550)-Sar$_3$-(DArg)$_2$);
and (SEQ ID NO: 63)
-C$_i$-S-F-[Aze]-Y-[hR]-C$_{ii}$-V-Y-Y-P-D-I-C$_{iii}$-A-Sar$_3$-
(D-Arg)$_2$ ((06-550)-Sar$_3$-(DArg)$_2$ Aze3 HArg5), wherein Aze represents an L-azetidine carboxylic acid residue, hR and HArg represents an L-homoarginine residue, NMeR and NMeArg represents an N-α-methyl arginine residue, Sar$_3$ represents 3 sarcosine spacers and (D-Arg)$_2$ represents 2 D-arginine residues.

13. The peptide ligand according to claim 12, wherein the peptide ligand is attached to an antibody or a fragment thereof.

14. The peptide ligand according to claim 13, wherein the antibody fragment is selected from an antibody light chain constant region (CL), an antibody CH1 heavy chain domain, an antibody CH2 heavy chain domain, an antibody CH3 heavy chain domain, or any combination thereof, in addition to the one or more constant region domains.

15. The peptide ligand according to claim 13, wherein the antibody or a fragment thereof comprises a hinge region of an antibody.

16. The peptide ligand according to claim 15, wherein the hinge region comprises the region between the CH1 and CH2 domains of an IgG molecule.

17. The peptide ligand according to claim 13, wherein the antibody or fragment thereof comprises an Fc region of an IgG molecule.

18. The peptide ligand as defined in claim 11, wherein the modified derivative comprises replacement of a proline residue with an L-azetidine carboxylic acid residue, and/or replacement of an arginine residue with an N-α-methyl arginine or L-homoarginine residue.

19. A peptide ligand as defined in claim 4, comprising a peptide sequence of:

(SEQ ID NO: 63)
-C$_i$-S-F-[Aze]-Y-[hR]-C$_{ii}$-V-Y-Y-P-D-I-C$_{iii}$-A-Sar$_3$-
(D-Arg)$_2$ ((06-550)-Sar$_3$-(DArg)$_2$ Aze3 HArg5), wherein Sar$_3$ represents 3 sarcosine spacers, (D-Arg)$_2$ represents 2 D-arginine residues, Aze represents an L-azetidine carboxylic acid residue and hR and HArg represents an L-homoarginine residue.

20. The peptide ligand as defined in claim 1, wherein the pharmaceutically acceptable salt is selected from a hydrochloride or acetate salt.

21. The peptide ligand as defined in claim 1, which is specific for human, rat and/or rabbit plasma kallikrein.

22. The peptide ligand as defined in claim 21, which is specific for human plasma kallikrein.

23. The peptide ligand according to claim 1, wherein the peptide ligand is attached to an antibody or a fragment thereof.

24. The peptide ligand according to claim 23, wherein the antibody fragment is selected from an antibody light chain constant region (CL), an antibody CH1 heavy chain domain, an antibody CH2 heavy chain domain, an antibody CH3 heavy chain domain, or any combination thereof, in addition to the one or more constant region domains.

25. The peptide ligand according to claim 23, wherein the antibody or a fragment thereof comprises a hinge region of an antibody.

26. The peptide ligand according to claim 25, wherein the hinge region comprises the region between the CH1 and CH2 domains of an IgG molecule.

27. The peptide ligand according to claim 23, wherein the antibody or fragment thereof comprises an Fc region of an IgG molecule.

28. A pharmaceutical composition comprising a peptide ligand as defined in claim 1 in combination with one or more pharmaceutically acceptable excipients.

29. The peptide ligand as defined in claim 4, wherein the replacement of one or more amino acid residues with one or more non-natural amino acid residues comprises replacement of one or more polar amino acid residues with one or more isosteric or isoelectronic amino acids, and/or replacement of one or more hydrophobic amino acid residues with other non-natural isosteric or isoelectronic amino acids.

30. The peptide ligand as defined in claim 4, wherein the post-synthetic bioorthogonal modification of amino acids comprises modification of cysteine, lysine, glutamate, and/or tyrosine with suitable amine, thiol, carboxylic acid, and/or phenol-reactive reagents.

31. A method of treating an ophthalmic disorder comprising administering to a patient in need thereof a peptide ligand as defined in claim 1.

32. The method as defined in claim 31, wherein said ophthalmic disorder is an oedema in the eye.

33. The method as defined in claim 31, wherein said ophthalmic disorder is a disorder related to impaired retinal vessel permeability.

34. The method as defined in claim 31, wherein said ophthalmic disorder is an angioneurotic oedema.

35. A method of treating an ophthalmic disorder comprising administering to a patient in need thereof a peptide ligand as defined in claim 12.

36. The method as defined in claim 35, wherein said ophthalmic disorder is an oedema in the eye.

37. The method as defined in claim 35, wherein said ophthalmic disorder is a disorder related to impaired retinal vessel permeability.

38. The method as defined in claim 35, wherein said ophthalmic disorder is an angioneurotic oedema.

39. A method for inhibiting plasma kallikrein activity in a subject, the method comprising administering a peptide ligand as defined in claim 1.

40. A method for inhibiting plasma kallikrein activity in a subject, the method comprising administering a peptide ligand as defined in claim 12.

41. A method for inhibiting plasma kallikrein activity in the eye of a subject, the method comprising administering to the eye of the subject a peptide ligand as defined in claim 1.

42. A method for inhibiting plasma kallikrein activity in the eye of a subject, the method comprising administering to the eye of the subject a peptide ligand as defined in claim 12.

* * * * *